US011937876B2

(12) United States Patent
Schiffman

(10) Patent No.: US 11,937,876 B2
(45) Date of Patent: *Mar. 26, 2024

(54) SMART PHONE VISION TESTING SYSTEM

(71) Applicant: Neuro-Eye Diagnostic Systems, LLC, Houston, TX (US)

(72) Inventor: Jade S. Schiffman, Houston, TX (US)

(73) Assignee: Neuro-Eye Diagnostic Systems, LLC, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 17/807,075

(22) Filed: Jun. 15, 2022

(65) Prior Publication Data

US 2022/0304571 A1 Sep. 29, 2022

Related U.S. Application Data

(62) Division of application No. 16/225,069, filed on Dec. 19, 2018, now Pat. No. 11,369,263.

(Continued)

(51) Int. Cl.
*A61B 3/032* (2006.01)
*A61B 3/00* (2006.01)
(Continued)

(52) U.S. Cl.
CPC ............ *A61B 3/032* (2013.01); *A61B 3/0025* (2013.01); *A61B 3/066* (2013.01); *G06F 3/0482* (2013.01);
(Continued)

(58) Field of Classification Search
CPC .... A61B 3/00; A61B 3/02; A61B 3/06; A61B 3/08; A61B 3/10; A61B 3/14;
(Continued)

(56) References Cited

U.S. PATENT DOCUMENTS

D395,295 S   6/1998   Wanishi et al.
D501,210 S   1/2005   Cook
(Continued)

OTHER PUBLICATIONS

Ted M. Montgomery, "Visual Acuity", http://www.tedmontgomery.com/the_eye/acuity.html, [retrieved from the internet on Dec. 16, 2020], 5 pgs.

(Continued)

*Primary Examiner* — Jie Lei
(74) *Attorney, Agent, or Firm* — Spencer Fane, LLP

(57) ABSTRACT

A handheld smart phone includes programming for performing various vision-related tests. The smart phone includes a touch sensitive screen, microphone, speaker, other sensors, processor and persistent storage for execution of software, multiple communications network interfaces and other device interfaces. The display delivers vision tests and, together with the speaker, related audio instructions to a user. The user interacts with the vision tests by using tactile and audio commands to the device screen and microphone. The test results are assembled into a report that can be transmitted to persons of the user's choice, such as a care provider. The capability is included for transmitting results to the remainder of the system for storage, analysis, events, alerts for medical personnel's user treatment and multiple user population analysis.

22 Claims, 28 Drawing Sheets

Related U.S. Application Data

(60) Provisional application No. 62/607,317, filed on Dec. 19, 2017.

(51) Int. Cl.
*A61B 3/06* (2006.01)
*G06F 3/0482* (2013.01)
*G06F 3/04883* (2022.01)
*G16H 15/00* (2018.01)
*G16H 40/63* (2018.01)
*G16H 50/20* (2018.01)

(52) U.S. Cl.
CPC ......... *G06F 3/04883* (2013.01); *G16H 15/00* (2018.01); *G16H 40/63* (2018.01); *G16H 50/20* (2018.01)

(58) Field of Classification Search
CPC ......... A61B 3/024; A61B 3/032; A61B 3/036; A61B 3/066; A61B 3/028; A61B 3/041; A61B 3/0025; A61B 3/005; A61B 3/0091; A61B 3/0033; A61B 3/1015; A61B 3/1225; A61B 3/103; A61B 3/113; A61B 3/18; G06F 3/0488; G06F 3/0482; G06F 3/04883; G16H 15/00; G16H 40/63; G16H 50/20
USPC ....... 351/246, 222, 223, 203, 237, 239, 243, 351/244
See application file for complete search history.

(56) References Cited

U.S. PATENT DOCUMENTS

| | | | |
|---|---|---|---|
| D608,786 S | 1/2010 | Jasinski | |
| D618,695 S | 6/2010 | Bennett et al. | |
| D654,084 S | 2/2012 | Joseph | |
| D662,109 S | 6/2012 | Steele et al. | |
| D666,625 S | 9/2012 | Gilmore et al. | |
| D679,722 S | 4/2013 | Ray | |
| D682,848 S | 5/2013 | Aoshima | |
| D683,743 S | 6/2013 | Oshima et al. | |
| D684,162 S | 6/2013 | Aoshima | |
| D684,173 S | 6/2013 | Rytt et al. | |
| D687,839 S | 8/2013 | Narayanamurthy | |
| D688,682 S | 8/2013 | Talbot et al. | |
| D688,687 S | 8/2013 | Smith et al. | |
| D690,725 S | 10/2013 | Song et al. | |
| D691,154 S | 10/2013 | Talbot et al. | |
| D767,593 S | 9/2016 | Yao et al. | |
| D788,118 S | 5/2017 | Omata | |
| D791,781 S | 7/2017 | Donarski et al. | |
| 11,369,263 B2 * | 6/2022 | Schiffman | A61B 3/032 |
| 2011/0082704 A1 | 4/2011 | Blum | |
| 2018/0008142 A1 | 1/2018 | Garoon et al. | |
| 2018/0125352 A1 | 5/2018 | Schmid et al. | |
| 2020/0129059 A1 | 4/2020 | Schmid et al. | |

OTHER PUBLICATIONS

"Ishihara Test", https://en.wikipedia.org/wiki/Ishihara_test, [retrieved from the internet on Dec. 16, 2020] 4 pgs.

https://web.stanford.edu/group/vista/wikiupload/O/Oa/Ishihara.14.Piate.Instructions.pdf https://www.stanford.edu/search/?cx=003265255082301896483%3Asq5n7qoyfh8&cof=FORID%3A9&ie=UTF-8&q=ishihara.14.plate.instructions&sa=Search, 3 pgs.

The Amsler Grid; https://amslergrid.org/ [retrieved from the internet on Dec. 16, 2020], 5 pgs.

"The Amsler Grid", https://health.ucdavis.edu/eyecenter/pdf/amsler_grid.pdf, [retrieved from the internet on Dec. 16, 2020] 1 page.

Health Insurance Portability and Accountability Act of 1996, https://aspe.hhs.gov/report/health-insurance-portability-6and-accountability-act-1996 (previous https://www.hhs.gov/hipaa/for-professionals/security/laws-regulations/index.html) [retrieved from the internet on Dec. 17, 2020], 2 pgs.

Jitesh Rohatgi, "GDPR and healthcare: Understanding health data and consent", Mar. 2, 2018, https://www.pega. 7 ::om/insights/articles/gdpr-and-healthcare-understanding-health-data-and-consent, [retrieved from the internet on Dec. 17, 2020] 2 pgs.

What is Rest, Rest API Tutorial, https://restfulapi.netl, [retrieved from the internet on Dec. 17, 2020], 16 pgs.

"Jenkins (software)", https://en.wikipedia.org/wiki/Jenkins_(software), [retrieved from the internet on Dec. 17, 2020], 6 pgs.

http:/lwww.myvisiontest.com/about.php, [retrieved from the internet on Jan. 5, 2021], 1 page.

https://opensource.com/article/18/9/open-source-log-aggregation-tools, [retrieved from the internet on Jan. 5, 2021], 9 pgs.

* cited by examiner

200

```
User: Ric
Email: ric         @sanocloud.com        212
Phone:
Device SN: B67AEF40-AD02-4534-B249-S2E
NEDS Tests Start: Nov 13, 2018 02:34:56 ( GMT: -8.0 )      210    Identification Section      Mobile App
Test Elapsed Time: 4m 50s                                                Included on all reports Additional user/patient & care provider information    214
```

Survey – Glasses:                                          220    Surveys Results Section
NEDS SG Started Nov 28, 2018 06:02:06- Elapsed 0m 3s              These sections Included on all Single
NO | Q1: Has your vision become worse form the last test?              Test Sequence reports
NO | Q5: Do you know you need reading glasses but just
          don't have them?
NO | Q6: Do you think it is easier to read when you hold
          the reading material further away form you?
Age 53 – 54, 1965 year of birth
Visual Acuity: Left Eye (OS)                               230    Acuity Test Results Section
20/80 (logMAR 6)
NEDS LVA Started Nov 28, 2018 06:02:11- Elapsed 57m 14s
Color Vision: Left Eye (OS)                                240    Color Test Results Section
10 of 11 , (missed 1)
NEDS LCV Started Nov 28, 2018 07:00:04- Elapsed 0m 27s
NEDS 5-Grid Amsler: Left Eye (OS)                          250    5-Grid Amsler Test Results Section
NEDS LAM Started Nov 28, 2018 07:01:49- Elapsed 2m 18s

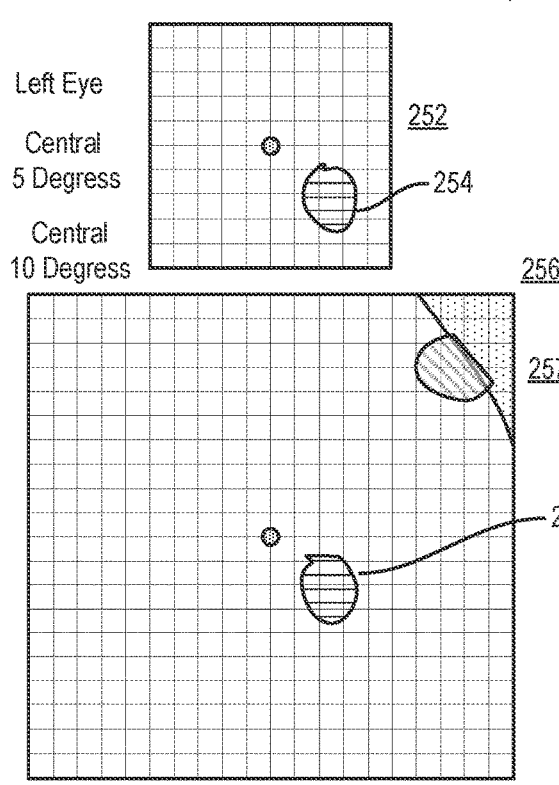

User friendly vision testing
App Store "EyeQTester"
www.eyeqtester.com
Neuro-Eye Diagnostic Systems LLC   210
   Houston, TX 77005 USA
HIPAA compliant, copyright 2015-2016

Survey – Glasses: 220
NEDS SG Started Nov 28, 2018 06:02:06- Elapsed 0m 3s
NO | Q1: Has your vision become worse form the last test?
NO | Q5: Do you know you need reading glasses but just
        don't have them?
NO | Q6: Do you think it is easier to read when you hold
        the reading material further away form you?
Age 53 – 54, 1965 year of birth
Visual Acuity: Left Eye (OS)
20/80 (logMAR 6)
NEDS LVA Started Nov 28, 2018 06:02:11- Elapsed 57m 14s
Color Vision: Left Eye (OS)
10 of 11 , (missed 1)
NEDS LCV Started Nov 28, 2018 07:00:04- Elapsed 0m 27s
NEDS 5-Grid Amsler: Left Eye (OS)
NEDS LAM Started Nov 28, 2018 07:01:49- Elapsed 2m 18s User: Ric    212
Email: ric          @sanocloud.com
Phone:
App Version 6.7.0 (100)                    Mobile App
Device SN: 054A9F78-2063-4864-8DB7-D9BE
NEDS Tests Start: Nov 28, 2018 06:02:11
(GMT: -8.0 )
Test Elapsed Time: 63m 27s 214
Additional user/patient care provider information 230  Visual Acuity: Right Eye (OD)
     20/50 (logMAR 4)
     NEDS RVA Started Nov 28, 2018 06:59:30-
     Elapsed 0m 17s
240  Color Vision: Right Eye (OD)
     10 of 11 , (missed 1)
     NEDS RCV Started Nov 28, 2018 07:00:39-
     Elapsed 0m 19s
250  NEDS 5-Grid Amsler: RightLeft Eye
     NEDS F Left Eye Central
5 Degress Central
10 Degress

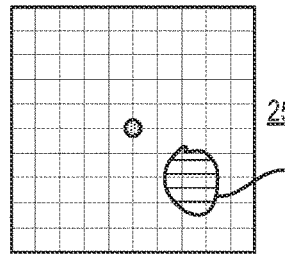
252
254
256

Right Eye

Central
5 Degress

Central
10 Degress

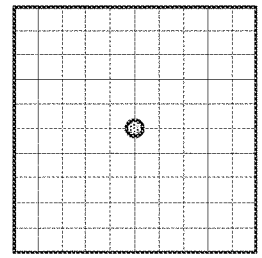

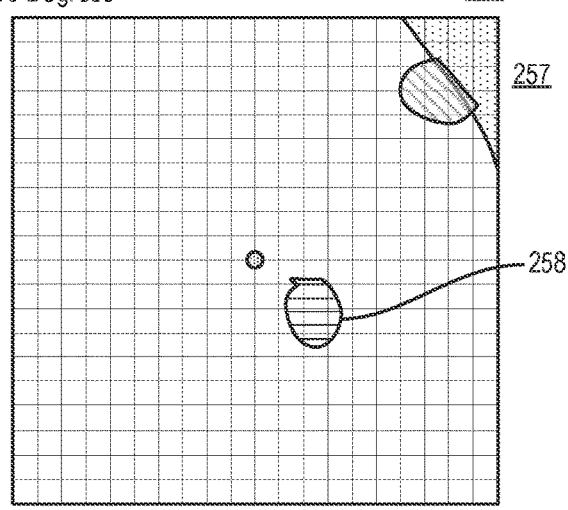
257
258

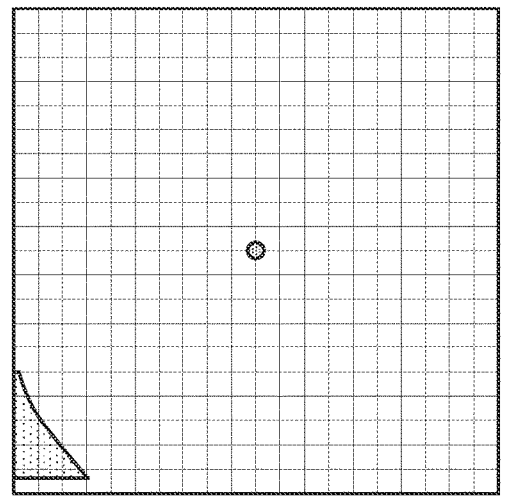

FIG. 2A2

300 Multiple Sclerosis InHome Monitoring – Single Test Sequence Report
NEDS MS Tools Results on: Jane Doe
Single Text Date on JANUARY 19, 2016 at 08:15 cst –
Report Date 3/10/2016 at 17:20 cst

| PRIOR | BACK | NEXT |

RIGHT EYE - OD
NEDS Digital Near Vision:
20/15 LogMAR: -1 High Contrast score by user
20/25 LogMAR: 2 Medium Contrast score by user
20/80 LogMAR: 6 Low Contrast score by user
NEDS Digital Color:
6 of 11 plates not recognized by user
NEDS Full 5-Grid 20x20 Amsler:

310 Identification Section
    Included on all reports
312                        Server
    Care Provider ID: 9999999999
314 NEDS Audit ID: 1457829151
    Medical Rec ID: 999-99-9999

330 Acuity Test Results Section
    (Test fpr Eye vision defects)

340 Color Test Results Section
    (Test fpr Eye vision defects)

350 5-Grid Amsler Test Results Section
    (Test fpr Eye vision defects)

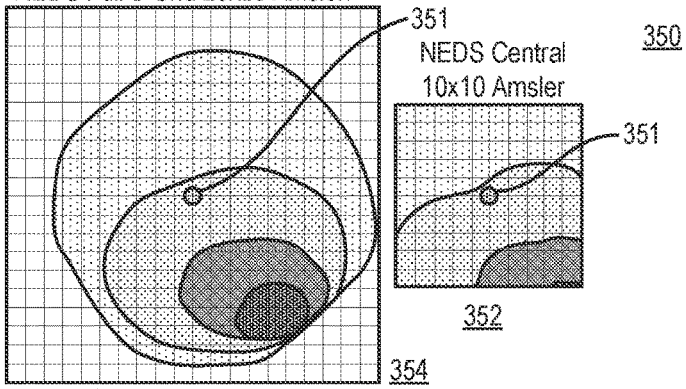

351
NEDS Central
10x10 Amsler
351
352
354

Area Affected as reported by user:
  199 / 400 50% of total area
Densities of affected areas:                356
  Light Gray:   112 / 199 56 % of effected area
  Medium Gray:  55 / 199 28 % of effected area
  Heavy Gray:   22 / 199 11 % of effected area RIGHT HAND    (Dominant Hand)
NEDS Digital 2 Finger Tap (2 trial average)
4 taps below (baseline is 73 taps in 30 seconds)
5 percent rhythm deviation
3 percent target deviation
NEDS Digital 9 Hole Peg (2 trial average)
3 seconds below (baseline is 186 seconds)
0 pegs failed to move
No tremor deviation (baseline is low tremor)
3 added boundary touches (baseline is 2 touches)

360 Dexterity Test Results Section
    (Test for Hand fine motor skill defects)

Gross Motor Test Results Section
MOBILITY                    370
NEDS Digital 25 Foot Walk (2 trial, out and back)
No elapsed time deviation (baseline is 45 seconds)
7 percent gait rhythm deviation
3 percent stager deviation Mental Test Results Section
COGNITIVE    380
NEDS Digital SDM Symbol Digit Modalities
         (2 trial average)
3 symbols below (baseline is 68 symbols in 90 seconds)
0 percent matching accuracy deviation (baseline is
         98% accurate)

Disclosure: All Events are presumed and not proven until confirmed by a health care professional who specializes in these conditions

FIG. 2B1

Server

Left Eye

Acuity Test Results Section 331
(Test fpr Eye vision defects)

Color Test Results Section 341
(Test fpr Eye vision defects)

5-Grid Amsler Test Results Section 351
(Test fpr Eye vision defects)

LEFT EYE - OS

NEDS Digital Near Vision:
20/15 LogMAR: -1 High Contrast score by user
20/15 LogMAR: -1 Medium Contrast score by user
20/15 LogMAR: -1 Low Contrast score by user
NEDS Digital Color:
0 of 11 plates not recognized by user NEDS Full 5-Grid 20x20 Amsler:

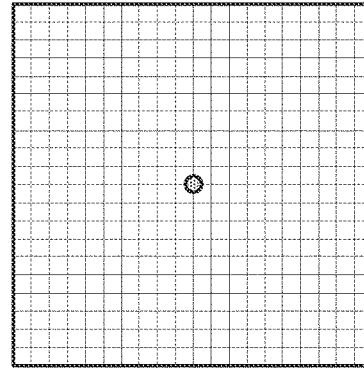
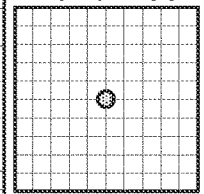

NEDS Central 10x10 Amsler
353
355

Area Affected as reported by user:
D / 400 00% of total area
Densities of affected areas:  357
N/A Dexterity Test Results Section 361
(Test for Hand fine motor skill defects)

LEFT HAND  (Non-dominant Hand)
NEDS Digital 2 Finger Tap (2 trial average)
4 taps below (baseline is 73 taps in 30 seconds)
5 percent rhythm deviation
3 percent target deviation
NEDS Digital 9 Hole Peg (2 trial average)
 3 seconds below (baseline is 186 seconds)
0 pegs failed to move
No tremor deviation (baseline is low tremor)
3 added boundary touches (baseline is 2 touches)

Disclosure: All Events are presumed and not proven until confirmed by a health care professional who specializes in these conditions

FIG. 2B2

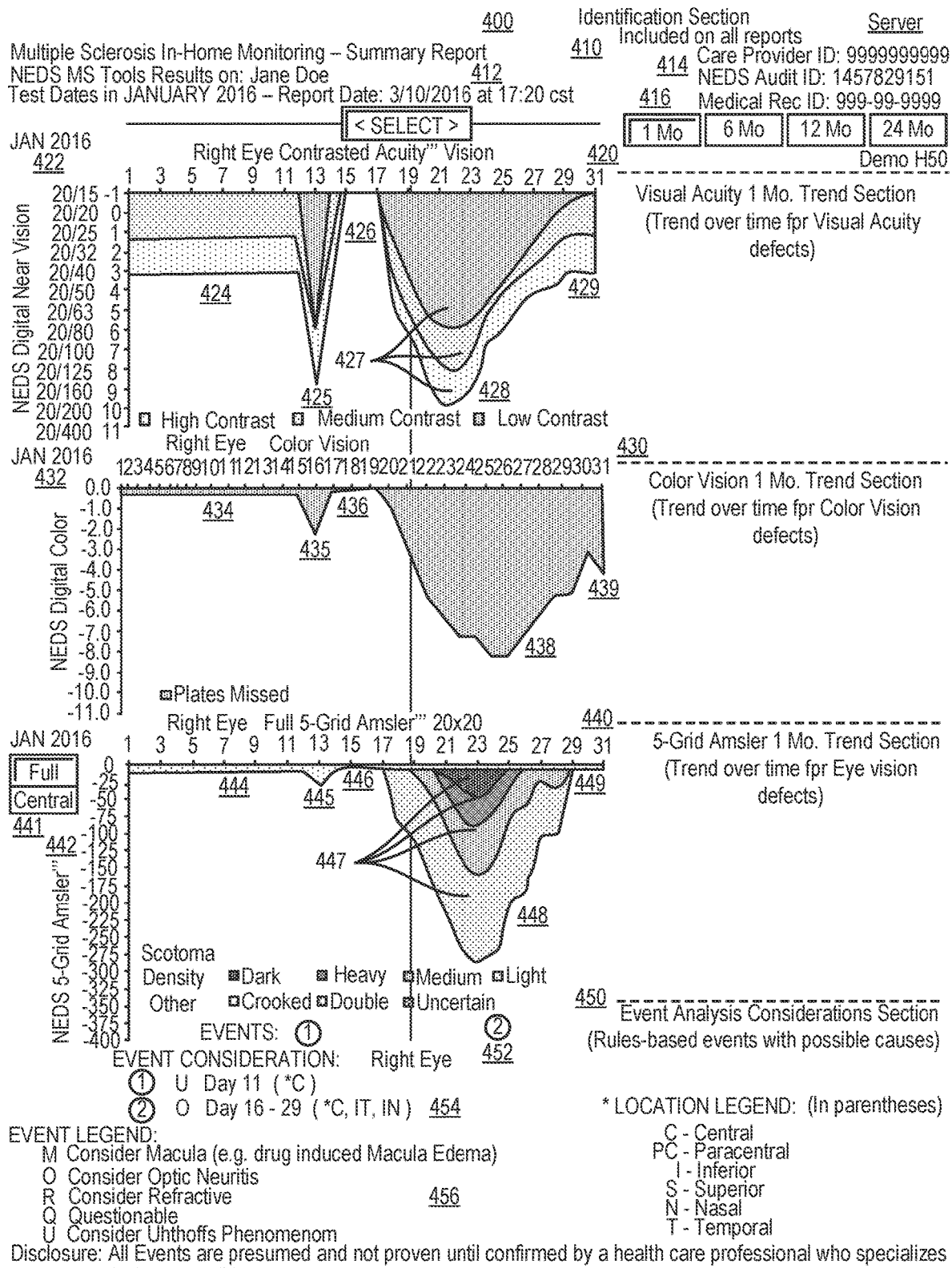
FIG. 2C1

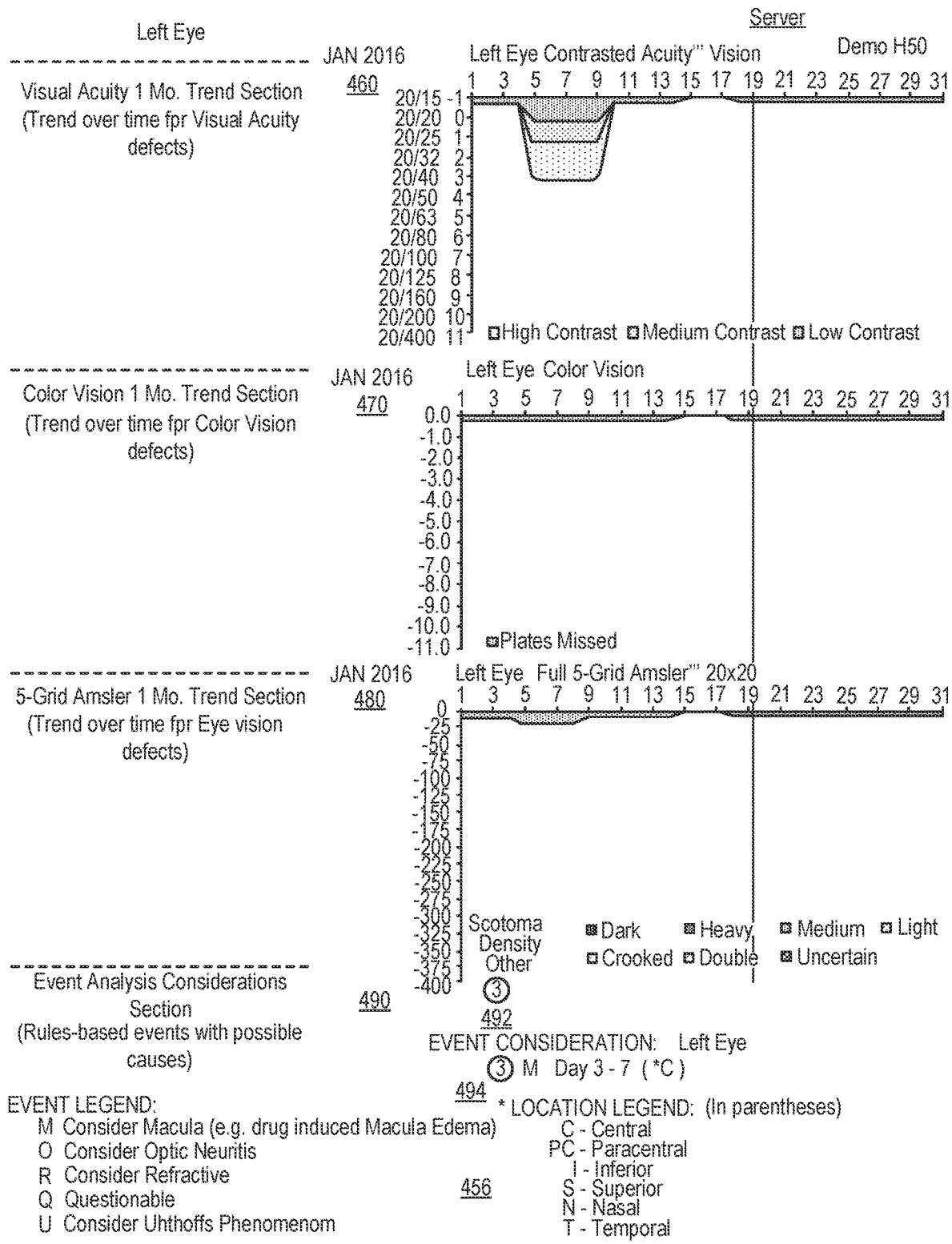
FIG. 2C2

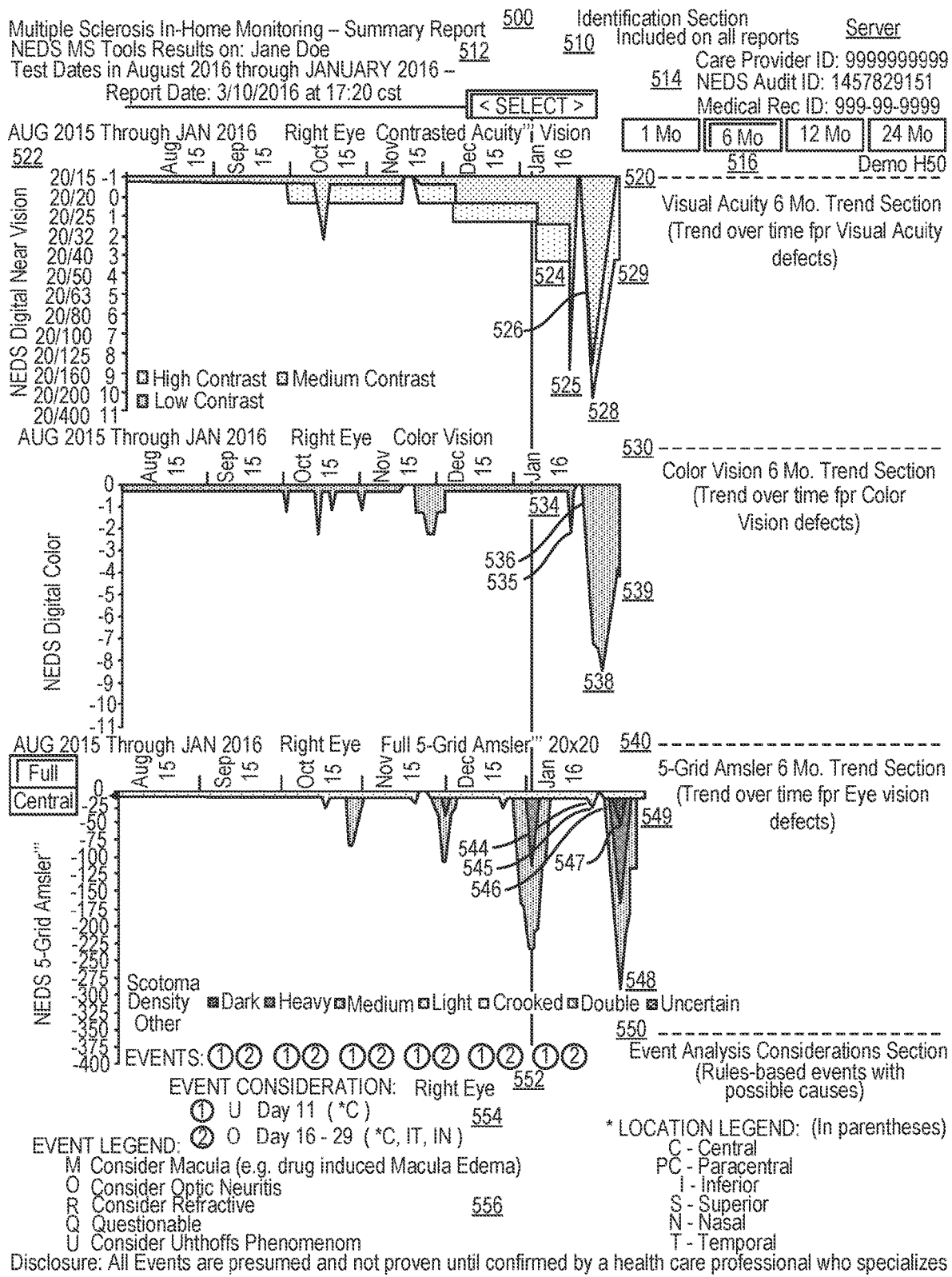
FIG. 2D1

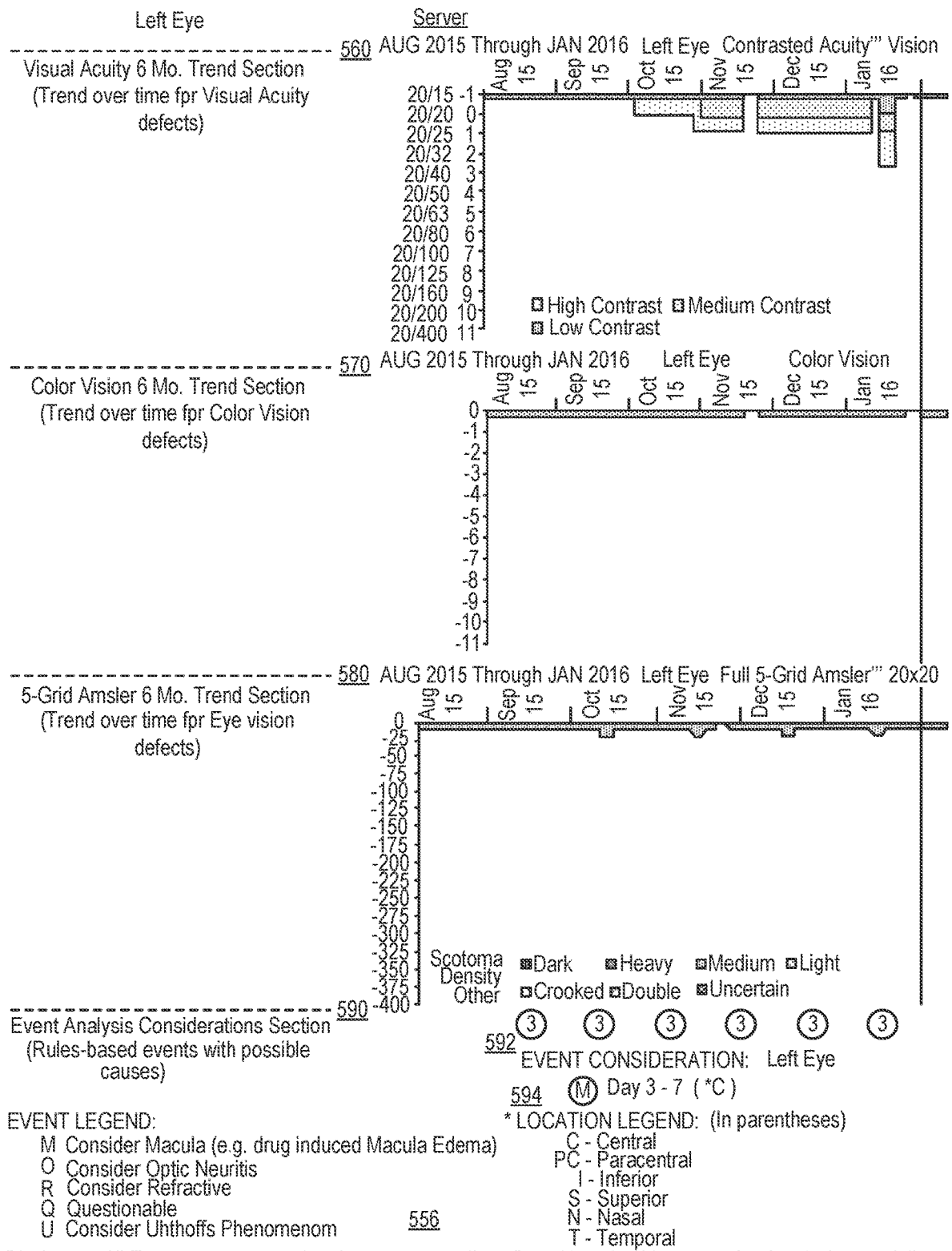
FIG. 2D2

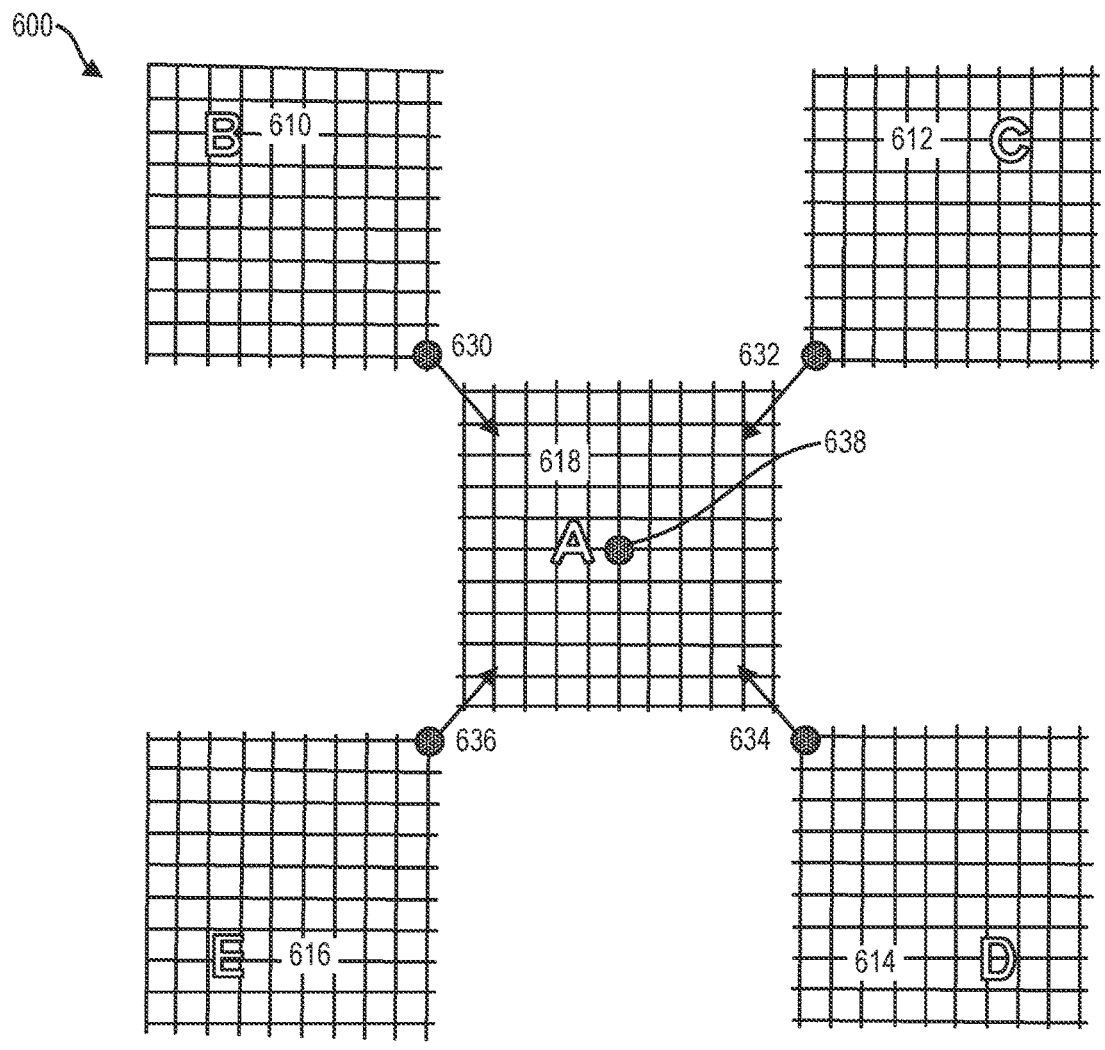
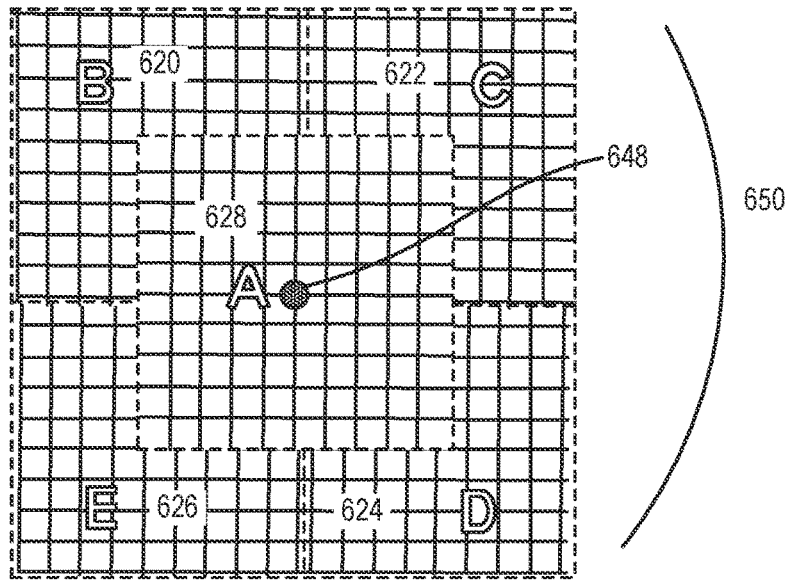
FIG. 3A

SMART PHONE VISION TESTING SYSTEM

CROSS-REFERENCE TO RELATED APPLICATIONS

This application claims priority from U.S. application Ser. No. 16/225,069 entitled SMART PHONE VISION TESTING SYSTEM, filed Dec. 19, 2018, which claims priority from U.S. Application No. 62/607,317 entitled MULTI-PART EYE TEST GRID REPORT FOR MOBILE DEVICE, filed Dec. 19, 2017, the contents of which are hereby incorporated by reference.

TECHNICAL FIELD

This disclosure relates to techniques for the design and implementation of a system for assembling reports from the execution of vision and related tests on a mobile wireless device, including data storage, analysis and reporting. In particular, the recognition and control of medical eye defects can be facilitated by using a report constructed from the assembly of multiple images resulting from vision testing on a mobile wireless device, such as a smart phone, for use with individual users, medical practitioners and researchers of multiple-user populations.

BACKGROUND

Vision testing is performed today primarily through professional evaluation using a variety of simple and advanced medical diagnostic tools in professional hospital and clinic settings. Professional evaluation, however lacks an important capability to detect changes quickly and in the user's daily environment with the resulting failure of timely administration of medication and the performance of medical procedures. There are some vision diseases, such as diabetic retinopathy, age-related macular degeneration, and other vision diseases and side effects from pharmaceuticals where ongoing monitoring of vision is critically important. Such diseases and pharmaceuticals may become active at unpredictable times in ways that affect the eye. If these effects are not promptly detected and treated, they could result in an irrecoverable vision loss in a matter of weeks or even blindness. The normal practice of relying on routine visits every 4 to 6 months leaves the patient vulnerable to these undiscovered changes.

Adaptation of the user's personal smart phone with a system for vision testing can give users at all locations and all times the ability to conveniently monitor their vision, identify changes, and report results for rapid evaluation. The system includes techniques for assessment of the user's testing accuracy. Additionally, the system solves a critical problem found in other handheld user operated devices, namely, the problem of care provider data overload from receiving high volumes of user generated test results, namely, where a small number of results are immediately significant for the user's care, but where all results must be reviewed due to liability consequences. The ability of the system to do rules-based filtering of incoming tests based on care provider preferences and provide only the significant test results to the provider for prompt review is a major benefit to the care providers ability to use the system effectively.

BRIEF DESCRIPTION OF THE DRAWINGS

FIG. 2A1 is a simplified example of a vision-related report created by the Mobile App (MA) portion of this system showing one example of the current test results for one or both eyes formatted in one column for display on the user's smart phone screen.

FIG. 2A2 is a simplified example of a vision-related report created by the MA providing one example of current test results for one or both eyes formatted in two columns for user's smart phone printing or transmission to someone, for example user's eye care provider.

FIG. 2B1 illustrates one example of a report created by the server portion of this system including the user's current test results made directly available for review by the user's eye care provider. Illustrated here is the left column of the report.

FIG. 2B2 illustrates one example of a server report including the user's current test results made directly available for review by the user's eye care provider. Illustrated here is the right column of the report.

FIG. 2C1 illustrates one example of a server trend report including the user's one-month historical and comparative results and trends from previous and current tests made directly available for review by the user's eye care provider. An alternative for trend presentation provides a 30 day or longer sliding window. Illustrated here is the left column of the report.

FIG. 2C2 illustrates one example of a server trend report including the user's one month historical and comparative results and trends for direct review by the user's eye care provider. Illustrated here is the right column of the report.

FIG. 2D1 illustrates one example of a server trend report like FIG. 2C 1 however providing context over a six-month timeframe. Illustrated here is the left column of the report.

FIG. 2D2 illustrates one example of a server trend report like FIG. 2C2 however providing context over a six-month timeframe. Illustrated here is the right column of the report.

FIG. 3A illustrates solving the problem of performing the full size 10 cm×10 cm grid Amsler test on a typical smart phone with limited screen size.

DETAILED DESCRIPTION

The present disclosure provides a means and a method of reporting changes in the user/patient's vision that have been captured on a mobile device through routine self-administered vision-related testing. This convenient testing approach permits the user to use their own mobile device on a daily or perhaps alternating day basis to perform vision-related testing. The mechanisms for capturing vision-related testing information on the mobile device and the processes for assembling meaningful reports of the captured testing information together with patient related statistics or trends are described herein.

These reports can be printed on paper or transmitted electronically to the patient's eye care professional or other care professionals for evaluation and, if needed, immediate and/or timely in-clinic follow-up. This report method measurably improves the utility of routine visits by providing a reporting and alerting mechanism for early intervention, if needed, between routinely scheduled in-clinic eye care visits. Enabling early intervention when vision change is detected will minimize vision loss.

The system described herein also provides long-term storage, comparative analytics with prior tests and trend analysis, providing collection for both user specific results and multiple time-series data. This also includes user data aggregation into populations for research projects.

Figure 1A:
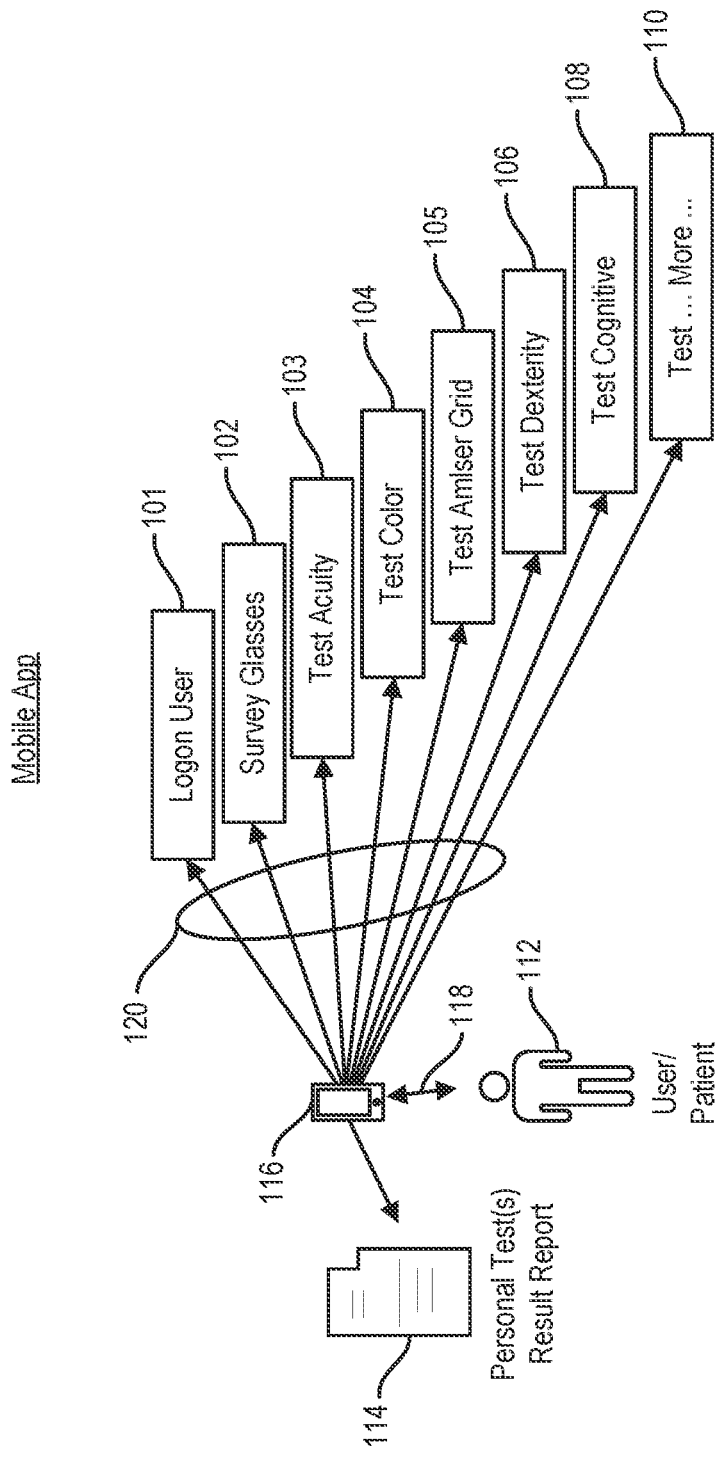
FIG. 1A is a schematic diagram illustrating a user/patient using a smart phone to perform vision tests on the user's own eyes and generate a report for personal use.

FIG. 1A illustrates an individual user/patient 112 in a personal location, such as their home, using a smart phone 116 configured with a mobile application ("MA") to perform vision-related tests 101-110 for the user/patient, collect results of the tests, and assemble a report 114 summarizing the results. In some places herein, we distinguish between a "user" of the MA for personal use and a "patient" utilizing the MA as directed by their eye-care provider to monitor their eye disease. The MA installed on smart phone 116 takes advantage of native features commonly found in smart phones, such as the Apple iPhone, Samsung Galaxy or Huawei Ascend, that help the user to perform the various vision-related tests. For example, the various smart phone features can be utilized to perform vision-related tests, e.g., tests 101-110, including common testing such as Acuity, Color, Amsler grid and others, as further discussed below. These tests are based upon known in-clinic tests that are implemented here in digital form to allow frequent reliable in-home testing and reporting. These test implementations include unique properties tailored to the advantages of the smart phone environment. The ability of the individual to conduct personal vision-related tests enables early detection of issues and prompt intervention by care providers to minimize vision loss.

Figure 1B:
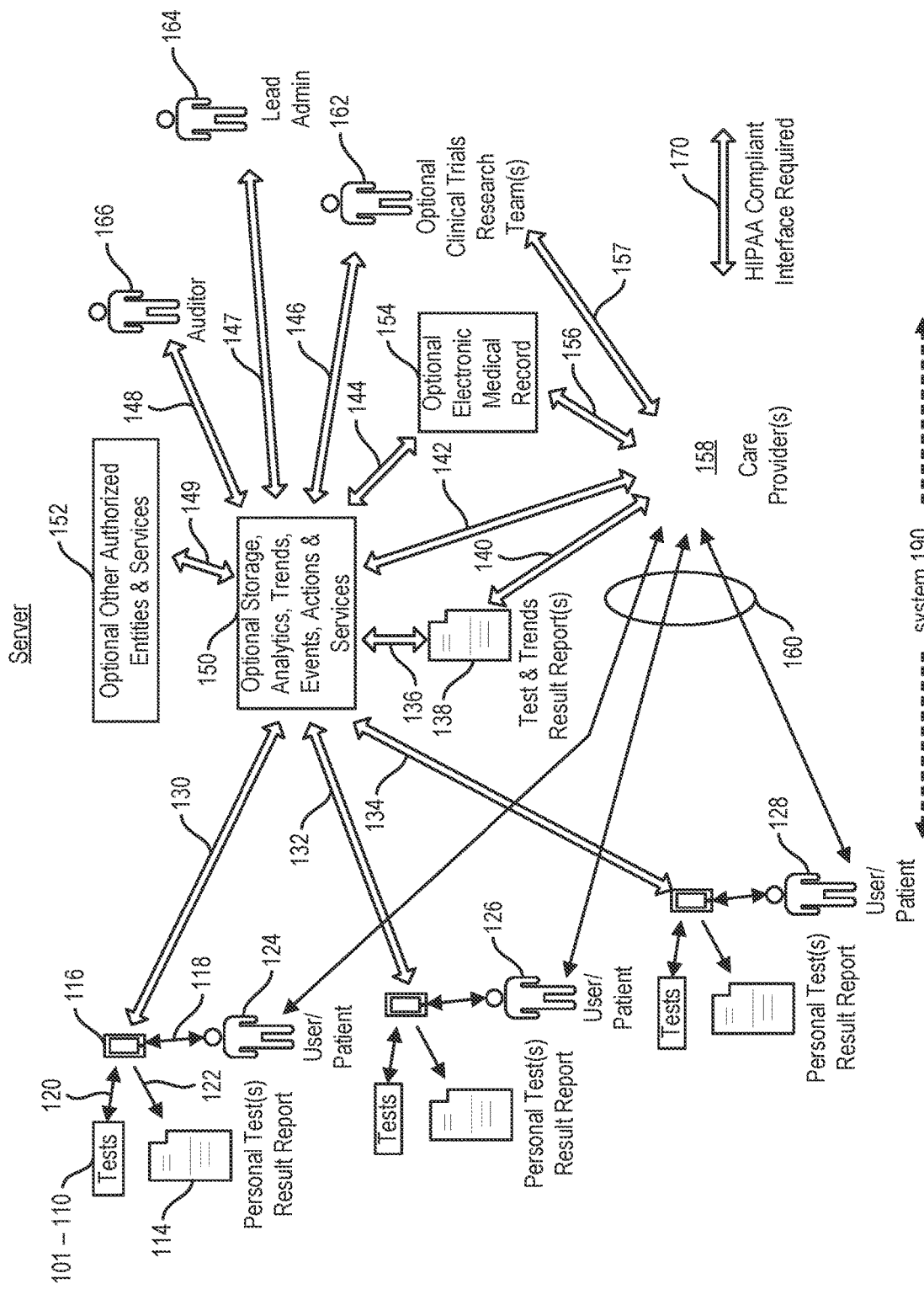
FIG. 1B is a schematic diagram illustrating one embodiment of a system in which the user communicates vision test results to the system for storage, analysis, trends, reports, events, actions, services and which is accessible to the user's care providers.

FIG. 1B shows a system 190 in which a number of users, such as users 124, 126 and 128, communicate the vision test results from their personal smart phones to one or more external resources, such as server 150, that may provide storage, analysis, trends, reports, events, actions, and other services, and which can be made accessible to the user's care providers 158 in accord with HIPPA regulations. The optional server-based storage, analytics, trends and reporting of test results provide important data flow reduction and highlighting of test anomalies for efficient use of care provider time, as further described below.

MA User Logon

Figure 4A:
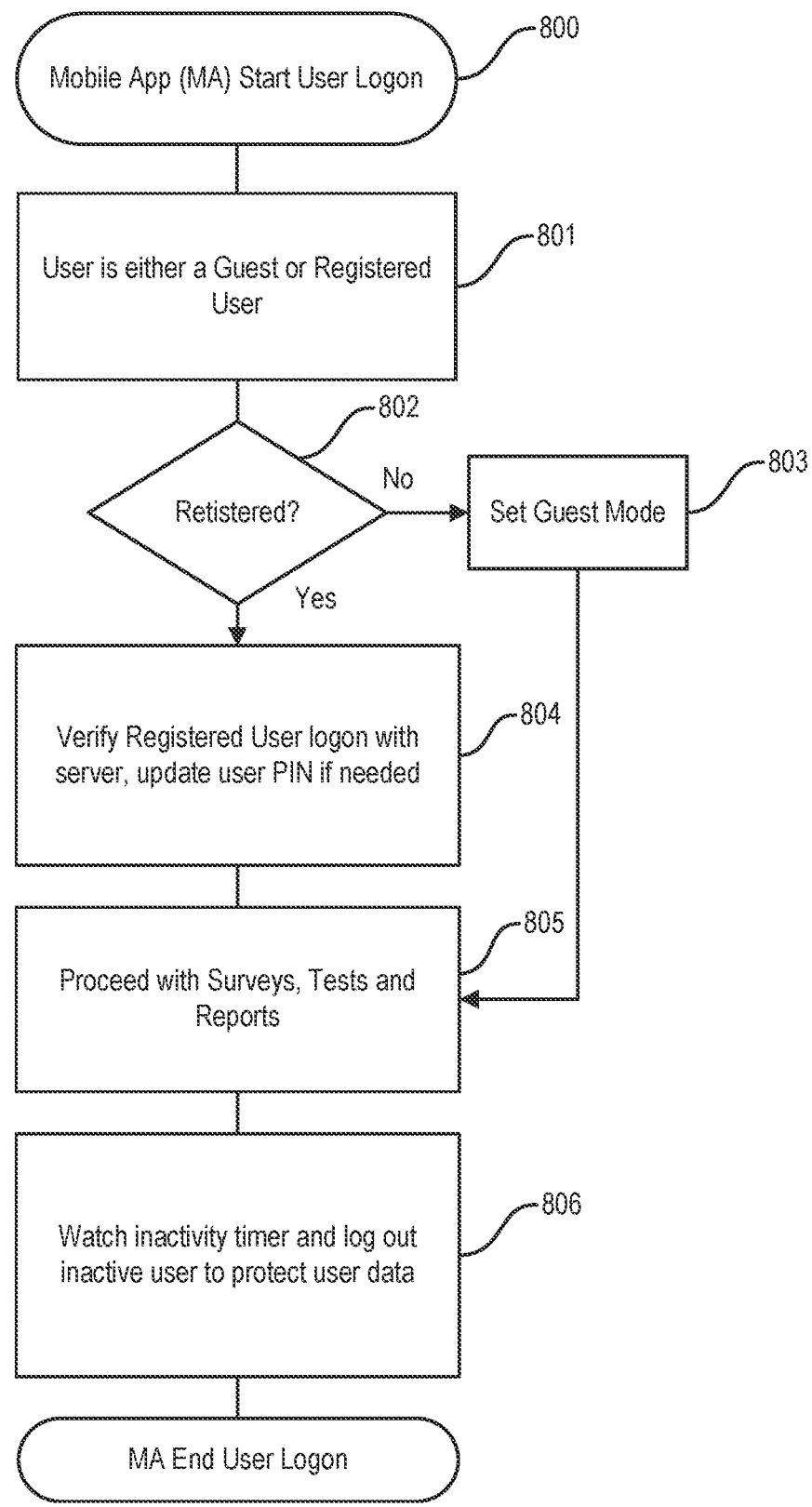
FIG. 4A shows Mobile App control flow for the User Logon sequence.

The MA may include a User Logon routine 101 to verify the identity of the user/patient 112 intending to use the MA on the smart phone 116 for vision testing 120. FIG. 4A provides a flow diagram of the logon process 101. At an initial screen, the user can provide an email address or choose "Guest User" in step 801. In step 802, the MA determines if this is a Registered User or Guest. If not a registered user, the MA sets Guest mode in step 803 and proceeds to surveys and tests in step 805. If the MA determines that the user is a registered user in step 802, then in step 804 the MA validates the email address together with the PIN entered by the user with the server 150 using the HIPAA compliant network connection 132 to the server. Once validated, the MA proceeds with surveys, tests and reports in step 805 described further below. In parallel, the MA monitors inactivity timeout or logout or other testing interruption flags in step 806 in order to protect the Registered Users data. For Guest user's testing interruption, the related data is erased.

An important feature to consider in interface design is the use by the non-technical elderly person or those with finger tremor, for example, through the design of button layout, size, persistence of finger touch (tremor), eliminating duplicate presses, and readability.

MA Survey for Glasses

The MA includes a Survey for Glasses routine 102 that asks whether the user's vision has changed, and determines whether the user currently wears glasses and is consistent with using them, which is an important consideration when evaluating the test results. The MA's survey mechanism supports responses that guide subsequent questions, and also, for the surveys or questions to be periodically updated via a connection 132 to the server 150.

Figure 4B:
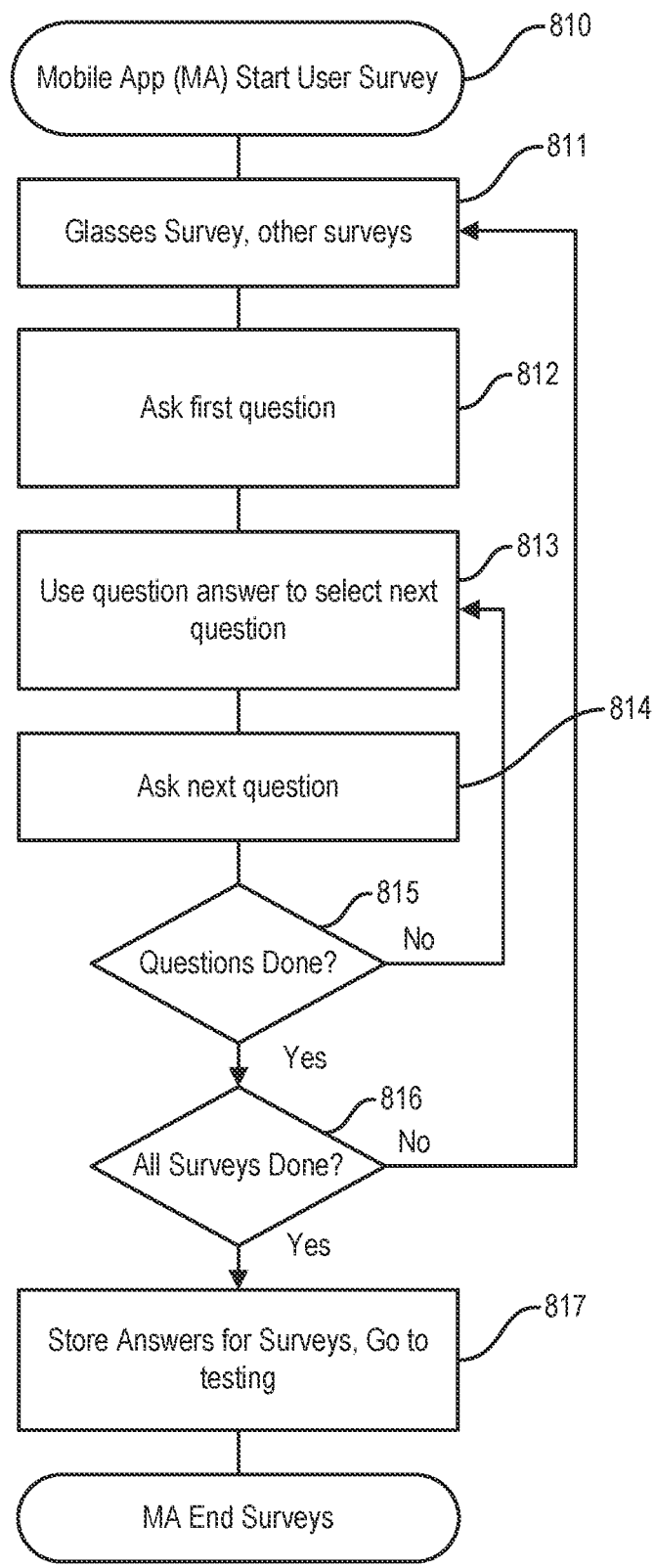
FIG. 4B shows Mobile App control flow for the Survey questions.

FIG. 4B provides a flow diagram of the Survey process 102. In step 811, the start time for this survey is noted and saved. In step 812, the initial question is asked, and in step 813, the question is answered and the next question is determined in step 813, then based upon the user's answer to the previous question, and the next question is asked in step 814. In step 815, the user answers the next question, and the MA checks to see that the necessary questions have been answered. If not, step 813 is performed again to ask the next question, and if yes, the survey is finished and the stop time for this survey is saved. Then the MA checks in step 816 whether all of the surveys have been performed, if no the MA goes to step 811 to perform another survey in the same manner, if yes in step 816 then all surveys are done. If so, then in step 817, the survey answers and start/end times are placed in persistent storage for registered users or in temporary storage for guest users, and the MA routine proceeds to the next test after step 837.

MA Visual Acuity

A Visual Acuity test 103 allows the user/patient 112 to perform this test for the chosen eye which proceeds to display a sequence of progressively smaller letters using the Sloan font (an optically correct font designed for this testing purpose and licensed for this use). To perform the test properly, the smart phone needs to be held at the correct distance from the eye being tested, in this case 40 cm (16 inches). Consistent distance from test to test is more important than exact distance. Visual Acuity is scored with reference to the Logarithm of the Minimum Angle of Resolution ("Log MAR"). Note for reference that Log MAR level 0 can be converted to "everyday language" as 20/20 vision, a common designation that people recognize but which is more difficult to use for optical calculations. For user convenience we display the Log MAR value adjusted by a multiplier of 10, thus a Log MAR value of 0.30 is displayed as a test score of "Log MAR 3". The correct Log MAR character size for display on the smart phone when held by the user at a particular distance from the eye, is calculated using standard optical formulas as described in the article by Ted M. Montgomery, Optometric Physician, entitled "Near Visual Acuity" available at web location: <http://www.tedmontgomery.com/the_eye/acuity.html>.

The test sequence proceeds by displaying a letter on the smart phone and having the user identify the letter by touching the corresponding choice button in the smart phone display with the same letter displayed upon it. When the letter is successfully identified, the size of the letter is reduced by one Log MAR step and the identification choice mechanism is repeated. When the user fails to identify a letter two times in the test, the resultant score from the test is the last successful Log MAR level accomplished. It may be a user with good vision will correctly identify all letters to the small size and Log MAR −1 becomes the user's score. It may also be the user is unable to identify any of the letters presented and then the user score is "worse than" the highest Log MAR level presented, currently Log MAR 11. Further our approach optionally incorporates variable contrast in the display letters which increases test sensitivity and provides further diagnostic data to the care provider.

Figure 4C:
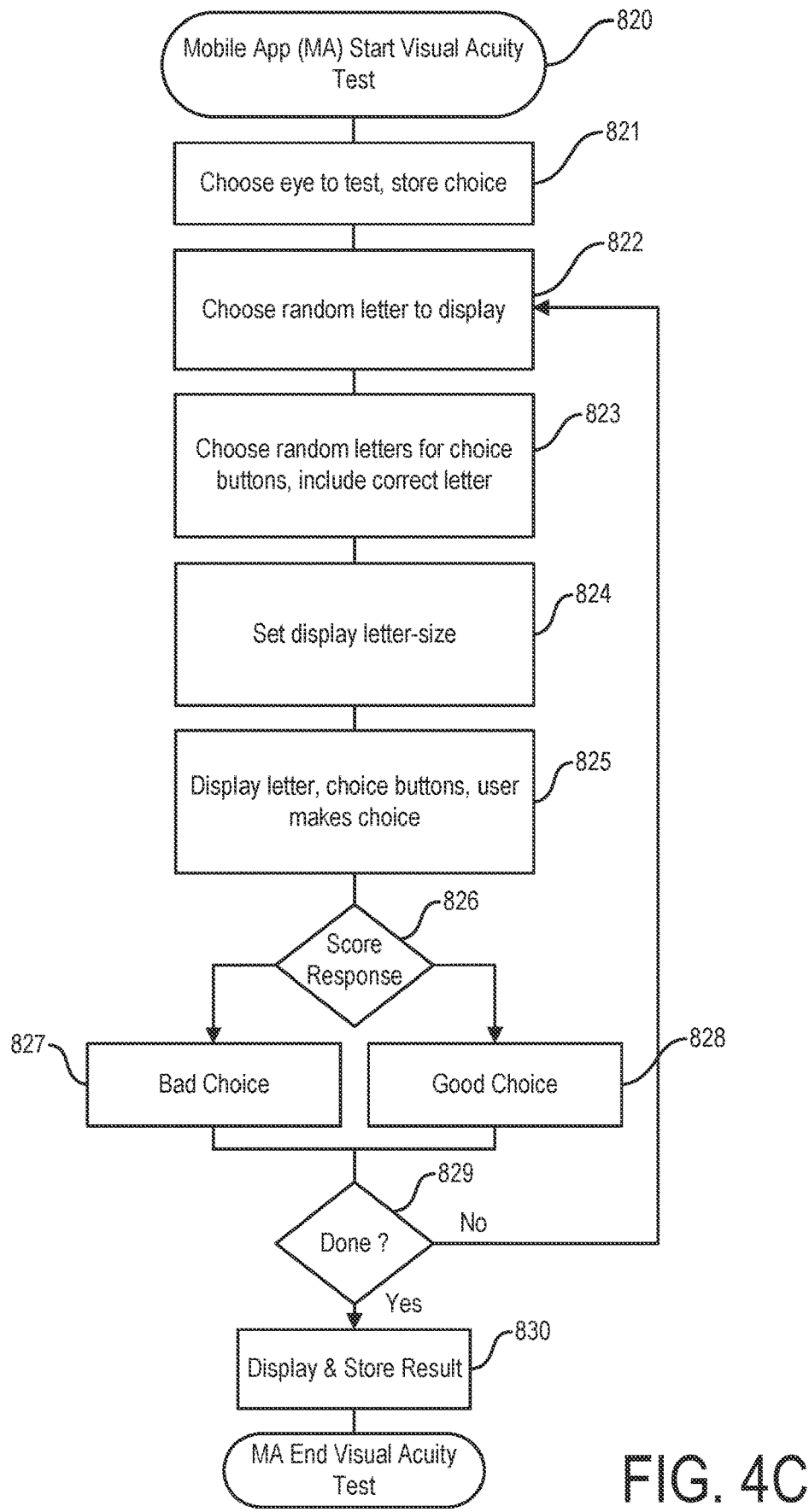
FIG. 4C shows Mobile App control flow for the Visual Acuity test.

FIG. 4C provides a flow diagram of the Visual Acuity test sequence, beginning with choosing the eye for testing in step 821, thereby prompting the user to cover the other eye and saving the test start time. A random Sloan font test letter is chosen in step 822. Next, the letters for display on the buttons are randomly chosen and randomly placed on the buttons of the smartphone in step 823, where one of the letters is the correct letter about to be tested. The Sloan test letter's font size is set in step 824, then the test letter and choice buttons are displayed on the user's smartphone in step 825, and the user makes a choice in step 825. The user's response is scored in step 826, and if the score indicates that the user has made a good choice (i.e., the user has correctly identified the letter), then in step 828 the test routine proceeds to reduce the font size to the next lower log MAR level. Then the process is reviewed to see if testing is done in step 829. If not, the process returns to step 822 to test with the smaller letter prepared in step 828.

If the user's response does not score well (i.e., the user did not correctly identify the letter) in step 826, then the process determines whether the user has incorrectly identified this letter twice (double verify mode) in step 827. If not, then the process prepares a different current size letter in step 827 to give the user another chance to identify the current letter. Then the process is reviewed to see if testing is done in step 829. If not, the process returns to step 822 to test with the letter prepared in step 827.

In the "Double verify" mode, each Log MAR level is verified twice in step 826, and selection by the user of two good choices causes the score to move down one log MAR level in step 828 and continue testing in step 829. However, with a second bad choice then step 827 ends the test. As the test ends, the end time and test results are stored, and the score is then displayed to the user in step 830.

MA Color Vision

The Color Vision test 104 displays a sequence of selected Ishihara's color plates for the chosen eye. An explanation of the well-known Ishihara plates can be found at the following links to web-based articles: <https://en.wikipedia.org/wiki/Ishihara_test> and <https://web.stanford.edu/group/vista/wikiupload/0/0a/Ishihara.14.Plat-e. Instructions.pdf>.

Commonly referred to as the "colorblindness" test, these test plates also provide diagnostic information for multiple other medical problems. As implemented in the MA, the plates have been selected to demonstrate certain abnormal characteristics familiar to eye care providers. The test proceeds with a randomized presentation of selected plates and randomized choice buttons that include the choice associated with normal color vision and additional choices that an eye care provider will associate with abnormalities.

Figure 4D:
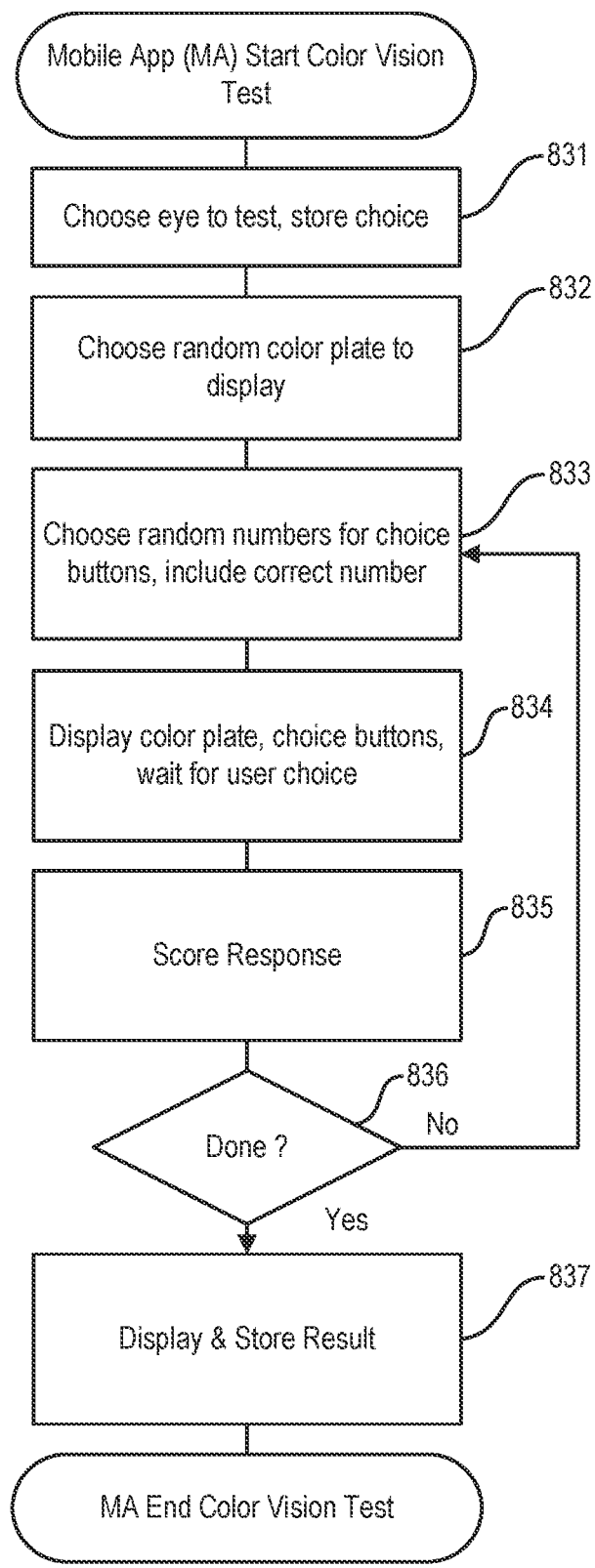
FIG. 4D shows Mobile App control flow for the Color Vision test.

FIG. 4D provides a flow diagram of the Color Vision test sequence, beginning with choosing the eye for testing, prompting the user to cover the other eye, and automatically saving the test start time in step 831. Standard Ishihara color plate 12 begins the test with randomized color test plate choices thereafter in step 832. The response button choices, including the "normal" and certain "abnormal" choices, are randomized in step 833. Then the test color plate and choice buttons are displayed and the MA waits for the user's choice response in step 834. The user's response is received and scored in step 835, and if still testing in step 836, the test cycle repeats with the random selection of one of the remaining color plates in step 832. When all of the plates have been displayed and scored, the test ends, the end time and test results are stored, and the score is then displayed to the user in step 837.

MA Amsler Grid

The Amsler Grid test 105 is a tool that eye care providers and individuals can use to detect vision problems resulting from damage to the macula (the central part of the retina) or the optic nerve. The damage may be caused by macular degeneration or other eye diseases or other diseases that affect the eye or by pharmaceuticals that may have side effects on the eye. The Amsler Grid is useful in detecting these problems and if found the user should promptly seek eye care. See the articles at <http://amslergrid.org/>; <https://health.ucdavis.edu/eyecenter/pdf/amsler_grid.pdf>; and http://www.myvisiontest.com/about.php.

The examples described herein are sized for a typical smart phone display, but could be sized for effective use on other displays while maintaining the required size square of 0.5 cm. The standard Amsler 10 cm.times.10 cm grid has squares of 0.5 cm size which properly used represent a one-degree area on the retina inside the eye. The correctly sized square helps eye care providers understand the accurate location of problems inside the eye. The test proceeds to display a unique sequence of 5 grids, as shown on FIG. 3A, with a vision Fixation Point (FP) located on each grid, the grids labeled A 618, B 610, C 612, D 614, and E 616. The first grid A represents the central 5 degrees of vision with a central Fixation Point (FP) 638, and the other four are each 5 degrees of vision in quadrants around the same central FP 638. The four quadrants in this example are illustrated for the right eye as: grid B 610 with superior nasal FP 630, grid C 612 with superior temporal FP 632, grid D 614 with inferior temporal FP 634, and grid E 616 with inferior nasal FP 636. These five grids are drawn separately are marked upon separately by the user, and then the grids are composited together into grid 650 to create a single 10 cm by 10 cm standard Amsler grid. This approach allows the creation of the standard Amsler grid using the smaller screen of the typical smart phone. The user's mark and categorization process using finger or stylus drawing on the screen and audio/response is described further in the section below.

Figure 3B:
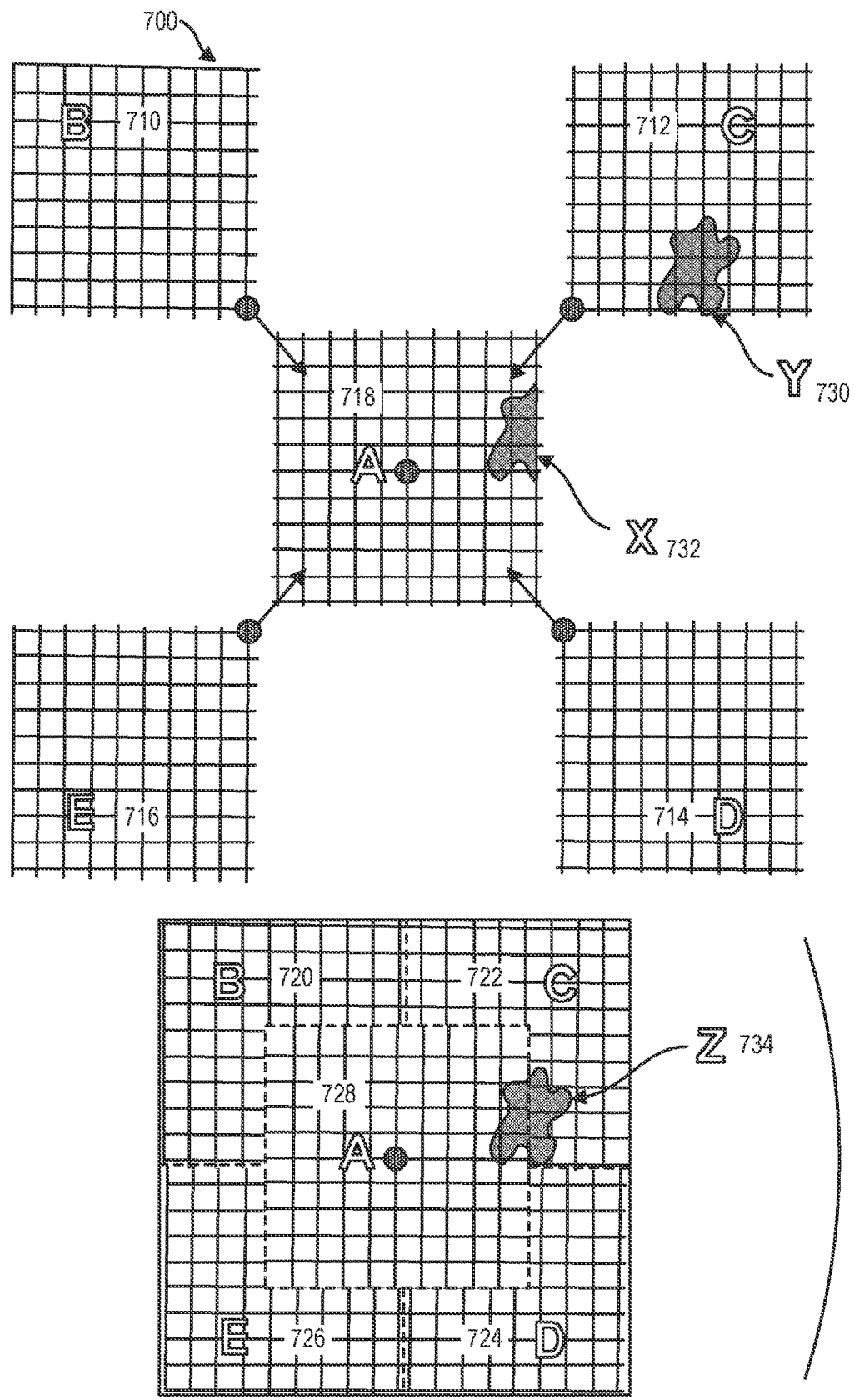
FIG. 3B shows that by solving the problem of performing the Amsler test on a typical smart phone, the additional capability of validating the accuracy of the users Amsler test is gained.

FIG. 3B shows how the 5-grid approach enables the validation of user marks on the screens where the central grid A 718 is overlapped by the 4 quadrant grids B, C, D, E to determine and score the user's grid marking consistency. For example, the user makes a mark "X" 732 on the central grid and then proceeds to complete the 4 quadrant grids with a mark "Y" 730 on grid C 712. When the test composites the 5 grids 750, the mark shows at "Z" 734 and the test also matches the marks "X" 732 and "Y" 730 to create a grid marking consistency score. All of the marks and matching score are provided to the eye care provider via the server 150 or on the user's report as discussed in the related section below.

Figure 4E:
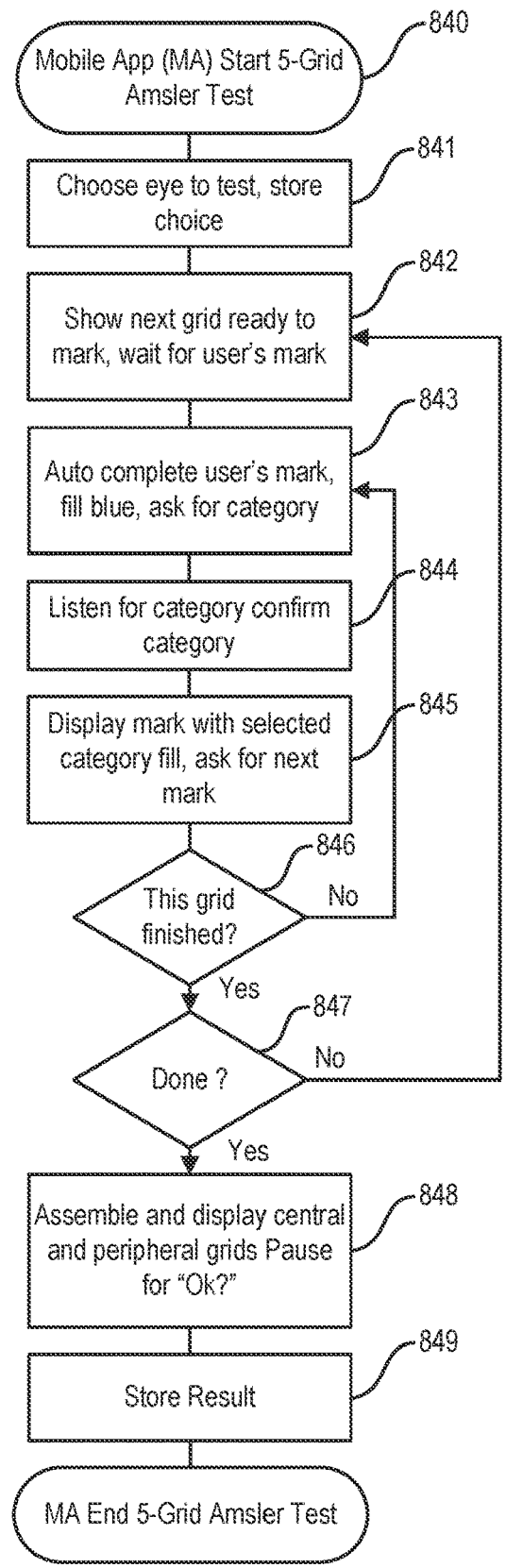
FIG. 4E shows Mobile App control flow for the 5-Grid Amsler test.

FIG. 4E provides a flow diagram of the 5 Grid Amsler test sequence, beginning with choosing the eye for testing, prompting the user to cover the other eye and saving the test start time in step 841. In this description reference is also made to FIG. 3B on document 700. Display of the central grid 718 begins the test where a grid with a central fixation point is displayed.

Note the successful Amsler marking depends on continuous focus at the fixation point, therefore a unique characteristic of this implementation is the use of audio/response to avoid user eye movement and maintain accurate grid marking. Uniquely, and for HIPAA privacy compliance, the audio/response feature is contained completely inside the Mobile App.

The fixation point is black with a pulsing white dot that indicates the user can mark on the grid with their finger drawing a shape representing any vision defects the user sees while focused on the fixation point. The marking process includes mark completion capability in case the users' mark end points are not closed or run off the edge of the grid. The users mark is shaded blue and the test's audio/response uses the speaker of the smart phone to verbalize a series of categories describing the nature of the mark 732 in step 843. These categories include "crooked", "double", "light gray", "medium gray", "heavy gray", "dark", "uncertain" and have the same meanings as used to identify manual markings on a standard paper Amsler grid. After the verbalization is complete the microphone of the smart phone is turned on and the central fixation point stops pulsing and turns solid indicating the user should respond verbally by choosing one of the categories. The test listens and identifies the user's response 844, confirming the response by repeating the category to the user through the smart phone speaker. The user is asked to verbally confirm the category through the microphone. If not confirmed, the user is given the opportunity to listen to the categories again and respond again. When confirmed, the users mark is filled with the category specific shading/marking in step 845. The use of audio response allows the user to maintain focus on the fixation point and prepare to make any additional marks with their finger in step 846. When the user has made all of the marks on this grid, they press the "Next" button to proceed to the next grid in step 847. After the user marks all five grids, or skips some with no marks, the user presses the "Done" button 847. The test finishes by assembling all five grids and displaying both the central grid and the assembled quadrant grids to the user, then waits for the "Ok" response in step 848. When the user confirms the grid display, the test ends, the end time and test results are stored in step 849.

MA Dexterity

The Dexterity test 106 requires the user 112 to place their finger on the screen and move icons from one position through an obstacle course to another position for nine iterations. In each of these iterations, the accuracy of the movement is measured by contact, or not, between the icon and the obstacles. As the iterations proceed, tolerance for icon movement is reduced so difficulty for accurate movement increases and is measured by the test.

MA Cognitive

The Cognitive test 108 requires the user to match two rows of presented information, touching the second row to indicate the choice, and where the presented information, typically a color, does not match the associated text, and where the choice row can match either the color or the text. This creates cognitive dissonance, and the number of correct and erroneous choices are measured by the test.

MA More Tests

The server 150 could add update the MA to add other tests of the user's capabilities to extend disease related testing features for in-home monitoring and reporting to care providers.

MA Personal Test Result Report

An example of a "Personal Test Result Report" 114 is created by the MA on the smart phone 116 and provided to the user as both an immediate report formatted for on-screen display as illustrated in FIG. 2A1 and as retainable report formatted for printing on paper or for sending as an attachment for digital delivery e.g. by email as illustrated in FIG. 2A2 The reports can be generated by the MA at any time in the testing sequence, and the generated report will contain time-stamped test results for recently completed tasks (typically within the last four hours) or indicate no results are available when a particular test has not been completed within the test window.

The report representations of test results have unique characteristics developed specifically for rapid interpretation by eye care providers. These test results are viewable both on screen as a single column FIG. 2A1 and optionally as a two-column display formatted for printing FIG. 2A2 that is available to both registered and guest users of the MA for emailing via the user's own email account to any one or more persons of the user's choice. HIPPA compliance is not required by regulations when the personal health information is entirely in control of the user on the user's own smart phone device and delivered using the user's own email account.

The MA's personal on-screen report display begins with results for the left eye of the user FIG. 2A1 having five distinct sections: The first section 210 is identifying information for the user 212 and optionally care-provider 214. The second section 220 is survey results. The third section 230 is Visual Acuity test results. The fourth section 240 is Color Vision test results. The fifth section 250 is the left eye 5-Grid Amsler plot results, including the central 5 Degree grid 252 in this case with the user's mark 254, then also the Central 10 Degree grid 256 in this case with the user's mark 258 corresponding to the same mark location as above 254. Other marks 257 show on the peripheral portion of the larger gird. Then scrolling farther down (not shown), the on-screen display would show the right eye results in the same format in the corresponding sections for Visual Acuity, Color Vision and 5-Grid Amsler.

The MA's personal printable format two column version FIG. 2A2 contains the same information described above for FIG. 2A1.

Figure 4F:
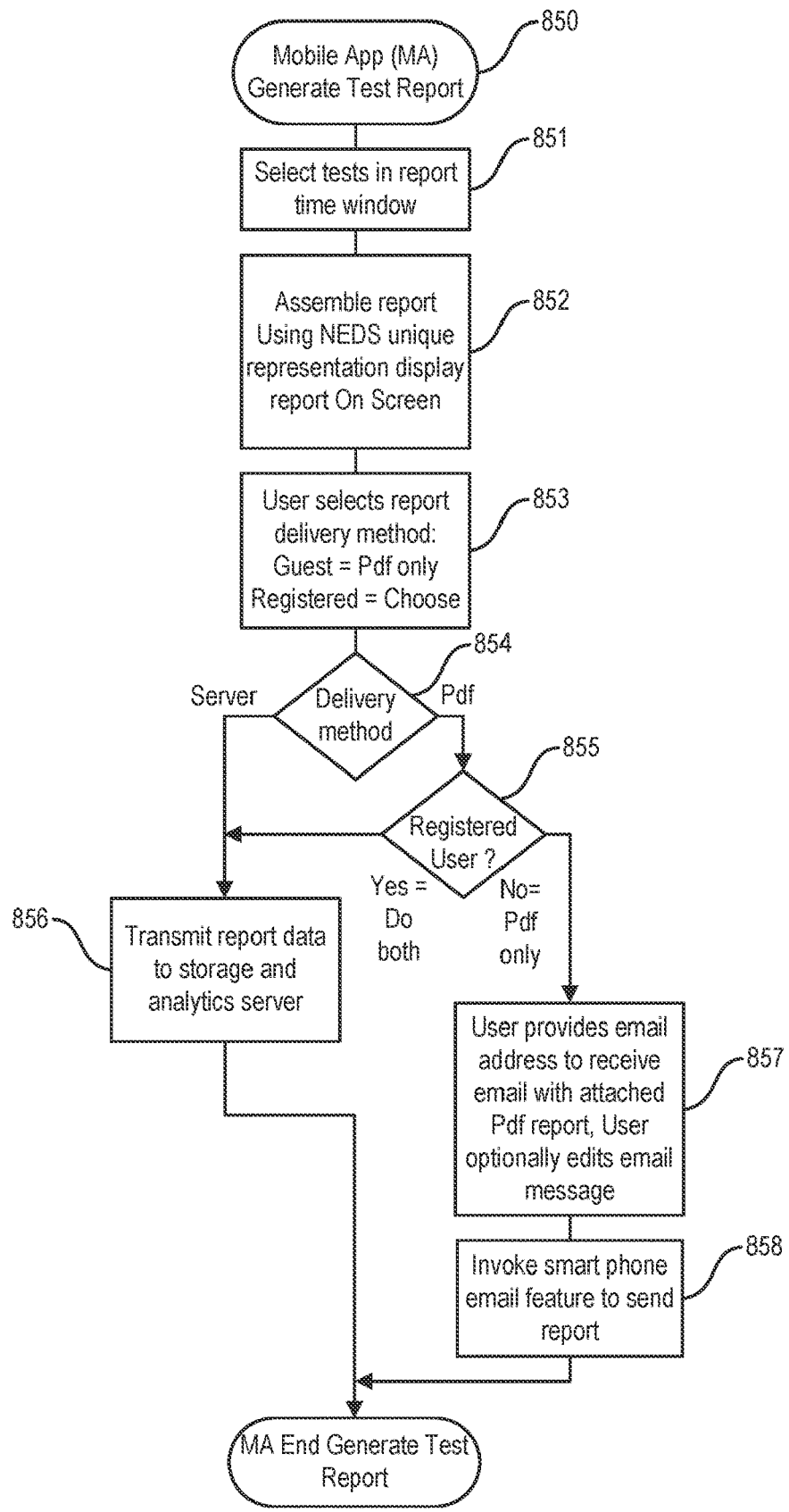
FIG. 4F shows Mobile App control flow for the Generate Test Report and for sending the report.

FIG. 4F is a flow diagram of the Personal Test Result Report by the MA. When requested by the user, the report generator uses test time-stamps to calculate the completion time of the last test taken and then establish a test reporting time window that includes, typically the prior four hours. The report will contain all test results occurring in that time window in step 851. The report is generated in step 852 in sections as described above typically including blocks 210, 220, 230, 240, and 250, as shown in FIG. 2A1 and FIG. 2A2. The report representations of test results have unique characteristics developed specifically for rapid interpretation by eye care providers. The report is initially viewable on the screen of the user's smartphone in step 852. After reviewing the report, the user optionally selects the delivery method in step 853. The Guest option is configured for hard copy MA report only, while the registered user can transmit to the server 150 and also create the MA report for device delivery. The Mobile App asks for preferred delivery method(s) in step 854 and verifies the user type in step 855. For server delivery, a HIPAA compliant connection is made to the server and the test results are delivered in step 856. For direct digital delivery the MA requests destination name and email information in step 857 then invokes the user's smart phone native email system with a preformatted email and digital report attached (typically a PDF digital format could be used). The user has the opportunity to add or modify the covering email text before pressing send for the email with the attached report in step 858.

MA Privacy, PHI, HIPAA and GDPR

The MA operates entirely within the user's own smart phone device where under HIPAA and GDPR regulations the user/patient is free to handle and distribute his/her own information as they see fit. Thus, for the user's own vision tests, the relevant test data is collected by the MA on the user's smart phone during a testing period, organized using relevant criteria and formatted into the user's MA report 114, as further detailed in FIG. 2A1 and FIG. 2A2. The MA generates the test results report for the user/patient's own use, all on the user's device.

Server Privacy, PHI, HIPAA and GDPR

In another embodiment, underlying any of a system 190 which includes server 150 based interactions are federal regulations for the security and privacy of the user's Personal Health Information ("PHI") (see Health Insurance Portability and Accountability Act of 1996 and subsequent regulations), <https://www.hhs.gov/hip aa/for-professionals/security/laws-regulations-/index.html>. In Europe, the General Data Protection Regulation (GDPR) is a framework for data protection laws that cover healthcare and related organizations (see the following article discussing GDPR and health care and related European Union GDPR regulations), <https://www.pega.com/insights/articles/gdpr-and-healthcare-understand-ing-health-data-and-consent>. Under these regulations, third parties handling the user's PHI are required to comply with user consent requirements and maintain the security of and access to such information according to user/patient's authorizations. Because this system in some embodiments transmits, stores the user's PHI and makes the PHI available to user authorized third parties, the system design incorporates the necessary design elements and operating processes that make the system HIPAA and GDPR compliant.

Server Interface for Mobile App (MA)

As briefly described above, FIG. 1B shows a system 190 which includes a server 150 for handling a number of users, e.g., users 124, 126 and 128, etc. Each user/patient uses their smart phone to take surveys and tests 101-110, generate a test report 114, and communicate test results over a HIPAA compliant communications link 130, 132, 134 to HIPAA compliant system 150, which provides storage, analytics, trends, events, communications, actions and the server may include optional services or interfaces. System 190 in turn provides care providers 158 with historical and current analysis of results 138 thereby allowing care providers to more effectively manage the user/patient's treatment options. For example, the device 116 of user 124 sends the collected test data and report(s) collected in the testing period using a PHI-secure communication link 130 to connect to a PHI-secure system 150, for example, a computer-based device such as a server.

Figure 5A:
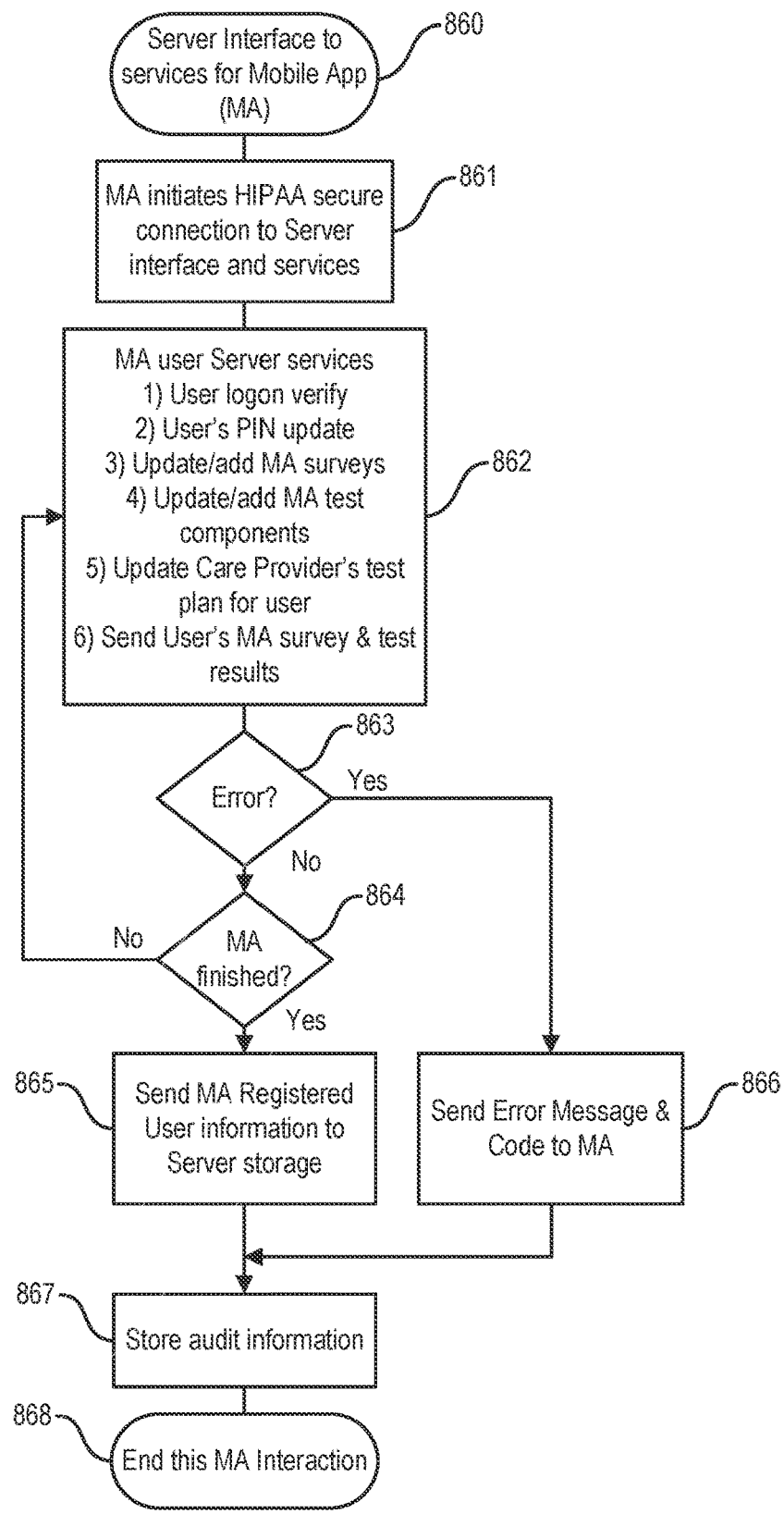
FIG. 5A shows Server control flow for the Server Interface services for the Mobile App.

FIG. 5A provides a flow diagram of an interface process 860 of the server 150 for services provided to the MA, for example, as installed on user device 116. In step 861, the MA initiates a HIPAA secure connection 130 between the MA 116 and the server 150. Each time the MA opens a connection to support the MA operation, the MA uses one or more of the server 150 services 862 that may include: [0068] 1) Server to validate a MA logon user email and PIN for user validation. The server 150 checks registered users and responds to the MA with either a) the user is valid/registered, or b) bad email or user not registered, or c) bad PIN, or d) error 863 (see below). [0069] 2) Server to update PIN for MA user's associated email. The server 150 checks registered users for MA user email and a) sends PIN update instructions to registered email and notifies MA PIN update email was sent, or b) tells MA email not recognized, or c) error 863 (see below). [0070] 3) Server to update/add MA user's surveys when MA sends user's survey version info and requests updates. Server 150 checks MA registered user's survey version info and responds a) no survey updates or adds, or b) sends for user the version x survey update or add package, or c) error 863 (see below). [0071] 4) Server to update/add MA registered user's test components when MA sends user's test version info and requests updates. Server 150 checks MA registered user's test component version info and responds a) no test updates or adds, or b) sends for user the version x test component update or add package, or c) error 863 (see below). [0072] 5) Server to update/add MA user specific test plan from Care Provider when MA sends user's test plan version info and requests updates. Server 150 checks MA registered user's test plan version info and responds a) no test plan updates or adds, or b) sends user's version x test plan update or add package, or c) error 863 (see below). [0073] 6) Server to receive survey and test results from MA for the registered user and responds a) results received, or b) error 863 (see below). [0074] Note: Error step 866, in all error cases the server 150 logs the error and provides a) action to take www, b) error description xxx, c) error code yyy, d) date ddd, time ttt, and unique error ID zzz, and e) supplementary information including help contact information appropriate for that error situation. The routine exceptions like "bad PIN" are handled above in the routine server 150 dialog with the MA. The remaining errors handled here are typically message version errors and malfunctions in the communication with the MA. For example, communication network errors, encryption errors for transmitted messages to/from the MA, message version errors where the version of the information sent from the MA is unable to be processed by the server 150. Version information assures the Survey and Test information are processed correctly. Communication and version exception handling is initiated here by notifying both the system administrator and the identified help contact for that user.

As each service request 862 is completed by the server 150, it checks to see if the MA is finished making requests in step 864. If no, service request processing continues by returning to step 862. If yes, the results of MA interactions are finalized in the server storage in step 865, and the server confirms to MA that the interaction is complete and disconnects in step 867. Every activity on the server 150 stores Audit information 867 (further described below with regard to Audit 166).

Server Storage for User Information

The HIPAA and GDPR compliant server 150 provides secure anonymized storage of User's PHI, and may include optional services or interfaces. To accomplish these features, the server 150 implements anonymization of User's data using keys, encryption and hashing techniques together with PHI-secure communication links 170. Highly scalable implementation techniques are used in recognition of the expected high volumes of test and analysis data and rapid access required for a highly responsive User Interfaces 136, 140, 142, 146, 147, 148 (detailed in subsequent sections below).

The server 150 can also be configured to aggregate and anonymize the test data and analytics results and to provide those test results via interface 146 for the use of clinical trial research teams 162 and their enrolled users/patients. To complete the security envelope for HIPAA/GDPR compliance, the server 150 depends upon the underlying secure data centers with physical and network access controls, security firewalls to prevent cooption by malefactors common on the Internet. The underlying platform configuration provided by the data centers include multiple physical devices and load balancers to maximize service levels and which are designed for secure data protection, load scalability, backup and recovery. Physical access to the equipment is monitored with cameras and security locks. Equipment service is only via security verified professionals and their access and work is logged into the audit system. Updates to the production server are all made by automated Jenkins deployment transfers (see https://en.wikipedia.org/wiki/Jenkins_(software)) from the secure staging version of the server where all changes to server features and underlying operating systems and services are verified before transfer into production.

Figure 5B:
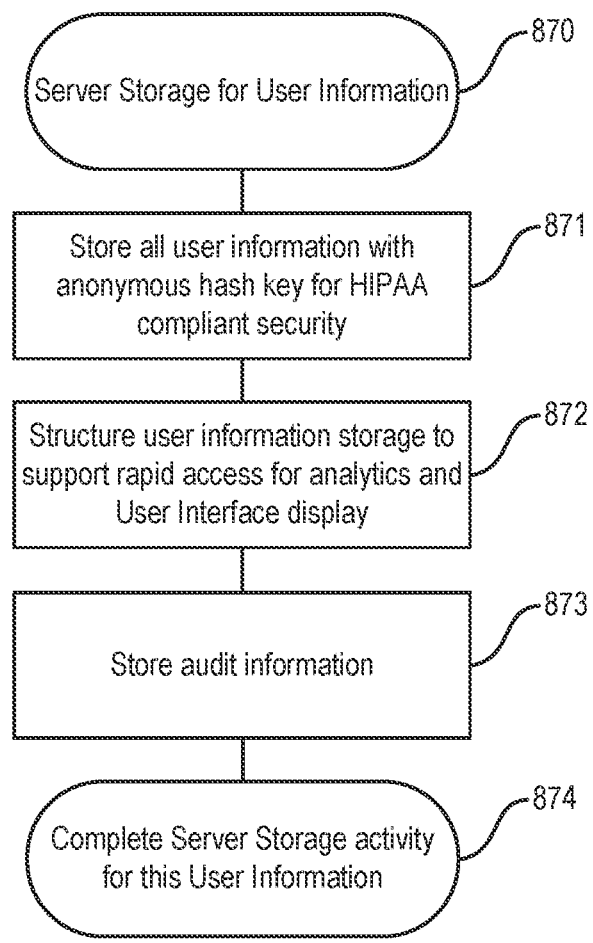
FIG. 5B shows Server control flow for the Server Storage for User Information.

FIG. 5B provides a flow diagram of user information storage using server 150. To store or access user information, the server 150 first converts the user key into an anonymous key using a hash technique in step 871. There are multiple data structures for various aspects of the user's data and derived analytics data. The data to be stored for the user is structured according to its particular purpose and then stored or updated into the data store using the anonymous key in step 872. The structures used to store the user's data are designed with human factors in mind with some derived elements pre-calculated in storage so the user interface provides rapid response in step 872. The accesses to the user data storage are entered into the audit log, and every activity performed on the server 150 stores audit information in step 873 (further described below with regard to Audit 166).

Server for Analytics and Trends

FIG. 1B shows an embodiment of this system 190 which includes the server 150 for Analytics and Trends and other services. System server 150 also performs ongoing real-time analysis of test data to create time series data and trend displays, such as sections 420 430, 440 on FIG. 2C1 and related displays on FIG. 2C2, FIG. 2D1, and FIG. 2D2, as well as related events and considerations in sections 450, 490, 550, 590. This report provides important context information about changes in the user's eye condition over time to the eye-care provider making recommendations for treatment or other action by the user. FIGS. 2C1 and 2C2 shows an example of a time series chart 400 displaying a one-month period by selecting button 416, and FIGS. 2D1 and 2D2 shows an example of a time series chart 500 displaying a six-month period by selecting button 516. 12-month and 24-month time frames are also available as is an alternative for time series presentation providing a 30 day or longer sliding window. These longer time frames provide additional contextual information for stability indicators or slowly changing trends that are not clear in shorter time frames.

Sections 420, 430, and 440 on FIG. 2C1 and corresponding sections of FIGS. 2C2, 2D1, and 2D2 implement the unique trend report display designed for rapid care provider recognition of problem areas and likely causes in just tens of seconds. The group of trend charts each display in a downward direction both the magnitude and problem category for each test result. All of the reports are designed with "up" is better and "down" is worse so the magnitude of problem areas, for example in graph extremes 428, 438, 448, and the types of problems displayed in the color coding 447 and texture 427 are immediately apparent in the display graphic. In one look for tens of seconds, the care provider is seeing all the related information from 50,000 to over 1,000,000 test points as described below. Because of the rapid display and pre-calculation design of the server 150, the eye care provider can also flip through multiple trend charts, look at individual test results and do multi-chart comparisons in seconds.

The MA single test result report 114 submitted by the user to the server 150 in this example for 3 different tests for both eyes contains from about 1,000 to 7,000 data points for charting and analysis. Therefore, the display 400 of trends for one-month of daily test reports for a single user results in representing somewhere between 30,000 and 210,000 data points on the report. Over a six-month period for the related report 500, the numbers are between 180,000 and 1,260,000 data points represented on the report. The system server 150 is designed to scale-up test processing for analytics to many tens of thousands of users and stores pre-computed analytics to support rapid report display 138 for care providers. On this system, to the largest extent possible, test data results are analyzed and precomputed results stored in a short time after the test results are received. In the case of the Amsler style grid test FIG. 2B1 for each eye, the analysis includes for each mark the user makes on the grid 352 and 354 (which can be irregular shaped and of any size):

1) Counting the number of marks by category (and also the grays as a category group);
2) Determining the size of each mark in fractional grid squares;
3) Totaling the number and coverage of grid squares by category (and also the grays as a category group);
4) Calculating the distance of each mark in millimeters between the mark's closest edge point and the fixation point 351;
5) Identifying any marks that touch or cross vertical or horizontal medial lines;

6) Matching marks made on the central grid 352 with marks made on the four-quadrant grids 354 to check for marking correlation as a score representing user marking consistency. For example: See the marks on the central grid 352 and the four-quadrant grids 354 in FIG. 2B1.

Analysis includes comparing these test report results with prior reports to compute trend lines, for example, on FIG. 2C1 see sections 420, 430, 440 and on FIG. 2C2 see sections 460, 470, 480. The results of these "precomputed calculations" are stored along with the original test data to support rapid display for care providers and for further analysis.

Figure 5C:
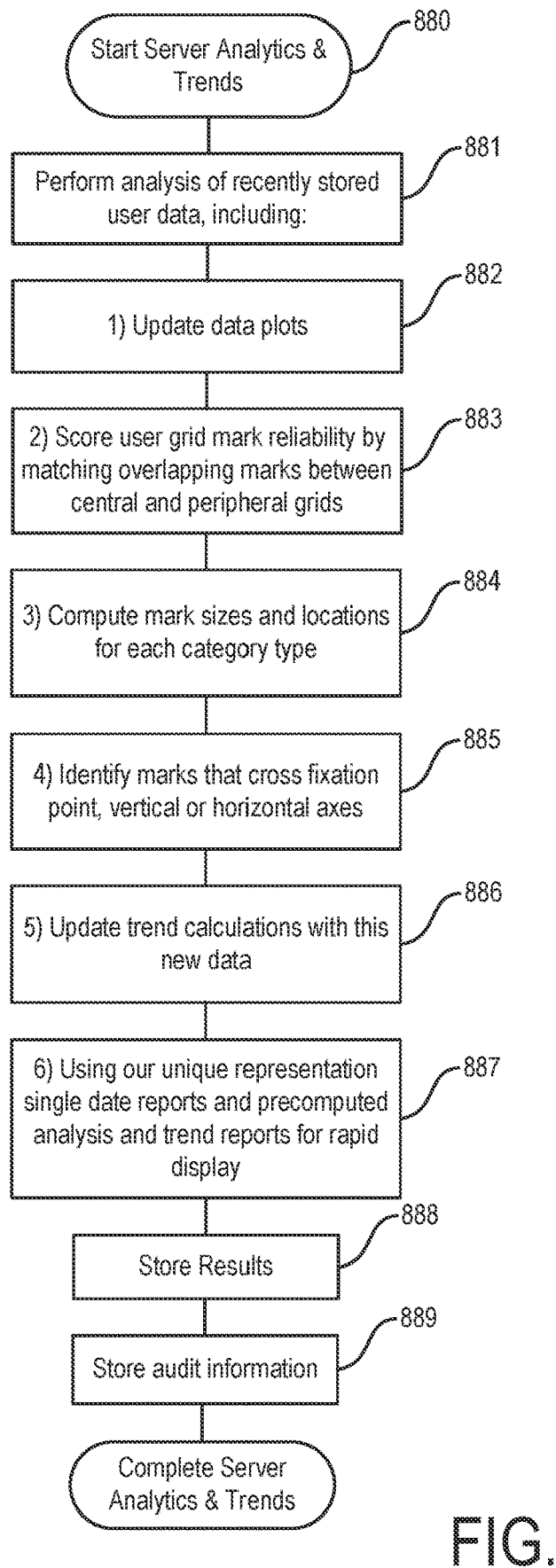
FIG. 5C shows Server control flow for the Server Trends and Analytics processing of stored information.

FIG. 5C provides a flow diagram of the Analytics and Trends process of server 150 for the user's test results. The just received User's test results report is obtained for analysis in step 881, including:

1) Update data plots in step 882;
2) Score grid mark reliability by matching marks between the central and four quadrant grids in step 883;
3) Compute mark sizes and locations for each category type and for the grays category group in step 884;
4) Identify marks that cross the fixation point, vertical or horizontal axes in step 885;
5) Update trend calculations with new data in step 886;
6) Using the unique trend display representations as discussed above, precompute single date reports and trend reports for rapid display in step 887;

The added results are stored in the server along with the user's test report data in step 888, and the accesses to the user data storage are entered into the audit log in step 889 such that every activity performed on the server stores audit information (further described below with regard to Audit 166).

Server for Events and Actions

System server 150 performs ongoing rules-based analysis of user's incoming test reports by comparing the just-received and processed information stored for that user with prior test data and trends for that user. Rules are configured in the server to compare various data elements, and if the conditions are met, the server generates either an Event or an Action. Events are notices communicated via interface 142 (further described below in Medical Group User Interface section) to the User's care provider about the event to enable care provider follow-up. Actions require User's care provider acknowledgement via interface 142 and identifying an action to be taken about the change in status together with the User. For example: a rule is established that if a User's Amsler grid mark moves more than two degrees (two grid squares) closer to the fixation point 351, an Action is initiated for contacting the User for a status check, to re-take the test, and if results are confirmed, a clinic visit. Rule parameter values can be a) default, b) adjusted for a particular User, c) assigned according to a group of Users with the same medical disease diagnosis, d) related to members of a particular Clinical Trial, or adjusted in additional ways.

When an Event or Action occurs based upon meeting the criteria of a rule, the notice of the Event or Action can go via interface 142 to one or more staff at the eye care provider's clinic. However, Actions are assigned and communicated via interface 142 to one specific accountable person (with copies to others) and that person must Act on the notices and that action is tracked along interface 142 by the server 150 system.

Figure 5D:
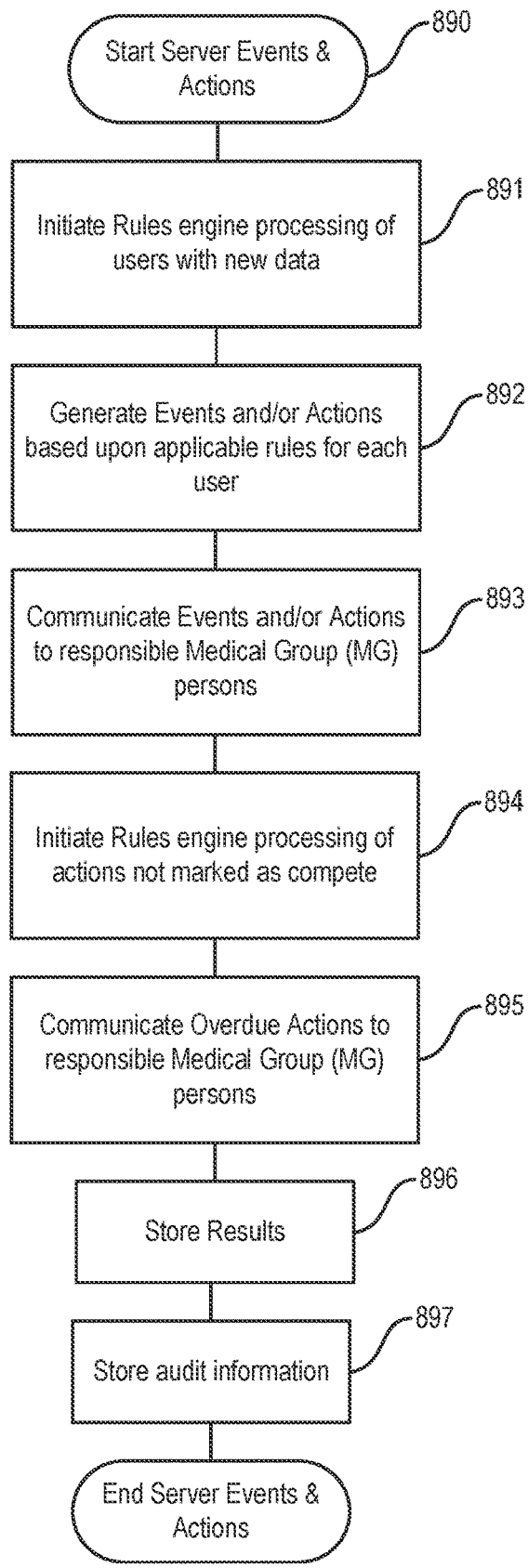
FIG. 5D shows Server control flow for the Server Rules based generation of Events and Actions.

FIG. 5D provides a flow diagram of the Events and Actions process for the user's test results using server 150. In step 891, the just-received, processed and stored User's test results report initiates the Rules processing of the new data. Events and/or Actions are then generated based upon applicable rules for the User in step 892, and the Events and/or Actions are communicated by interface 142 to responsible care provider (Medical Group) persons in step 893.

The rules processing continues to identify previous Actions not yet marked as complete and overdue in step 894. Further communication by interface 142 is made for overdue Actions to responsible care provider (Medical Group) persons in step 895. The Results in User's data and in Event/Action processing are stored in queues in step 896. Once again, entered into the Audit log are a) accesses to the user data storage; and b) any related Events or Actions, such that every activity on the Server stores Audit information in step 897 (further described below with regard to Audit 166).

Server Medical Group (MG) User Interface

As shown on FIG. 1B, the Medical Group (MG) User Interface (MGUI) 142 together with the server 150 Tests & Trends Result Report(s) 138 are the care provider's (and care provider's administrative staff) primary interface to information on the server 150. Notices of Events and Actions are managed through the MGUI. The Reports 138 include the User's single test report shown on FIGS. 2B1 and 2B2 as provided via the server 150 to the care provider 158 (it is a replica of the version of the report generated on the Mobile App augmented with additional MA test results (if any, for example Dexterity 360, Mobility 370, or Cognitive 380) and care provider identification information 314. The Reports 138 include examples of time series and trend charts as shown on FIGS. 2C1 and 2C2 for a one-month or 60-day period as selected by button 416 and on FIGS. 2D1 and 2D2 for a six-month or 180-day period as selected by button 516. Button options for generating 12-month and 24-month reports are also provided. The elements on the two examples are the same except for the time span the reports cover. The data presented in the examples are for both eyes and three tests.

In each example chart 420, 430, 440, the system design (discussed previously and further here) uniquely displays the data so that it is all oriented the same way for rapid, accurate, care provider interpretation. Data points near the top of the chart (such as data point 434) are favorable to the user status and points lower in a chart are unfavorable (such as data point 438). This chart data orientation is critical to the eye care provider's correct and rapid evaluation of the test results. In the provider's clinic setting, significant provider time is saved by this display approach. The charts 138 displayed by the system are accessed via interface 140 by care providers 158, and because of the server's precomputing step, the care provider can rapidly "flip" through different time periods using the active selector buttons 416, 441 as well as immediately drill down to the User's single test report on a particular day (see FIG. 2B).

A more detailed examination of FIGS. 2C1 and 2C2 illustrates one example of a report including the user's one month historical and comparative results and trends from previous and current tests, including results of the Acuity Test in graph 420, results of the Color Test in graph 430, and results of the 5-Grid Amsler Test in graph 440, as well as related events and considerations in section 450 of the report. In the Acuity graph 420, there are areas of stability 424, a short term worsening event 425, missing tests area 426, a longer term worsening event 428, and a return to prior vision acuity area 429. These same characteristics can be seen in the other two results for Color Test 430 and Amsler test 440. Note also that these two test's displays also distinguish the category of problem by using color coding and shading 427 and 447 in addition to magnitude for the severity. This report's display design provides important context information across time and tests about changes in the user's eye condition that can be rapidly evaluated for specific concerns and longer-term trends. This enables the care provided to see whether the current test results indicate an improvement or decline in user's status and the trend's rate-of-change as seen by the large deviations 428, 438, 448. This substantially improves the eye care provider's ability use status-guided considerations as shown in section 454 and to note events/actions 452 thereby enabling the eye care provider to make informed recommendations for care and other action by the user.

Another capability of the presentation design is the detail 427 in the Acuity Test results showing the effects of contrast in the test results and in region 427 of the Acuity Test. In a similar manner the detail in the 5-Grid Amsler Test showing the size and type of defect markings 447, where in this example, 75 percent of the user's visual field is impacted at the worst point in the event and 12 percent is completely black, as indicated by region 447. Very important details are thus quickly available to the care provider.

In a similar manner, FIG. 2D1 shows a longer time series and plainly shows serious deterioration in the User's vision over the past 180 days. This trend is not nearly as obvious when looking only at the one-month report in FIG. 2C1. The ability of the server 150 to quickly show the Reports 138 with important information and over different time frames at the click of a button 416 or button 516 means the care provider will make better decisions sooner than possible when only periodic in-clinic testing is used. This will likely improve care and preserve more of the patient's vision than current practice methods enable. PHI-secure communication links 140 and 142 are provided for communications with care providers 158. The User's own communication links 160 can be used by care providers to interact with their users/patients 124, 126, 128 (and more).

Figure 5E:
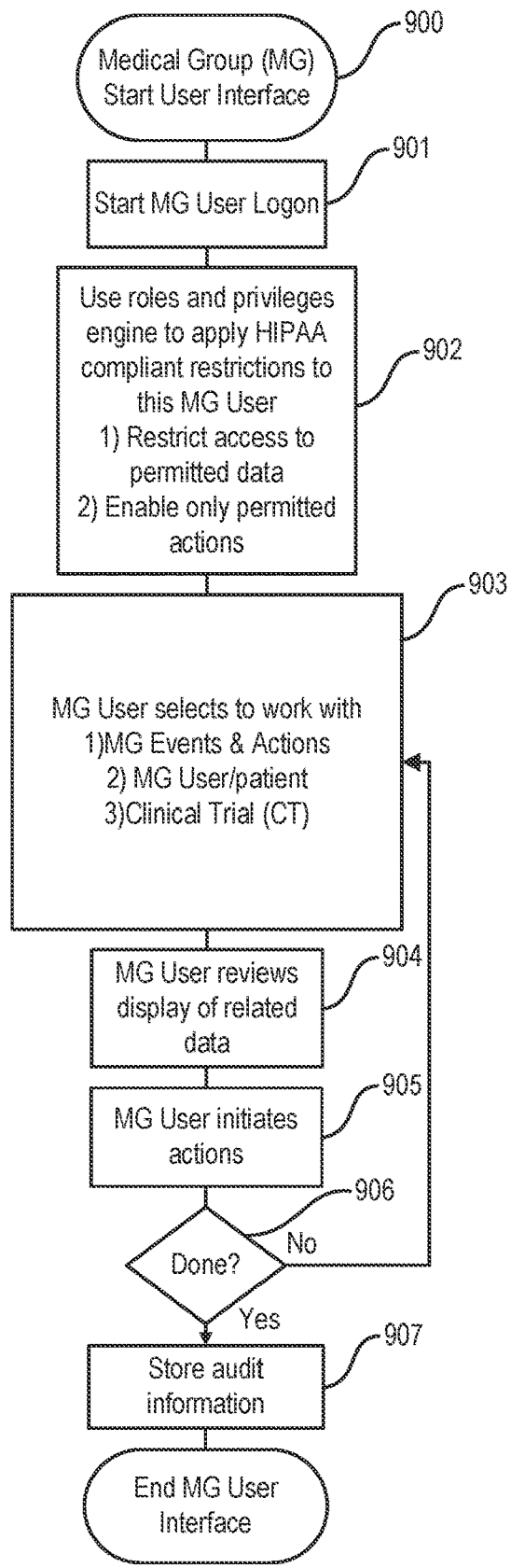
FIG. 5E shows Server control flow for the Medical Group (MG) User Interface.

FIG. 5E provides a flow diagram of the process for using the Server Medical Group (MG) User Interface 142. An eye care provider 158 or a member of their staff with necessary credentials can logon to the server 150 in step 901 using the server MGUI via HIPAA compliant communication link 142. As part of the logon process, the MGUI looks at the credentials of the person logging on for their assigned roles and privileges (which may be group participation related) to apply HIPAA compliant restrictions to this particular MG user that will 1) restrict access to permitted data and 2) enable only permitted actions, in step 902. Complying with the aforementioned roles and privileges, the MG User selects to work with 1) MG Events & Actions; 2) MG User/patient information; or 3) Clinical Trial (CT) activities, in step 903. MG User reviews the display of related data in step 904 and initiates actions as needed in step 905. If the MG User is not done in step 906, the process returns to step 903 to handle more activities. When MG User is done in step 906, or after an inactivity timer expires, the MG User logs out. Entered into the Audit log are a) accesses to user data storage; b) display of user data; c) any related Events or Actions; and d) any CT activities, such that every activity on the Server stores Audit information in step 907 (further described below with regard to Audit 166).

Server Clinical Research Organization (CRO) User Interface

Clinical Research Organization (CRO) User Interface (CROUI) 146 is the primary interface for the Clinical Research Organization (CRO) staff 162 (and CRO's administrative staffs) to information on the server 150. Notices of CRO Events are managed through the CROUI. The CRO works with anonymized data for a population of enrolled Clinical Trial (CT) patients. The server 150 can provide the CRO appropriate access to anonymized data for the CT population. Also, the server 150 can provide for the CT population aggregated time series and trend charts for multiple patients that appear similar to the reports shown on FIGS. 2C1 and 2C2 for a one-month period and on FIGS. 2D1 and 2D2 for a six-month period. The elements on the two examples are the same except for the time span the reports cover. PHI-secure communication links 146 are provided to CRO staff 162. A PHI-secure communication link 157 is also provided for interaction between CRO staff 162 and MG care providers 158.

Figure 5F:
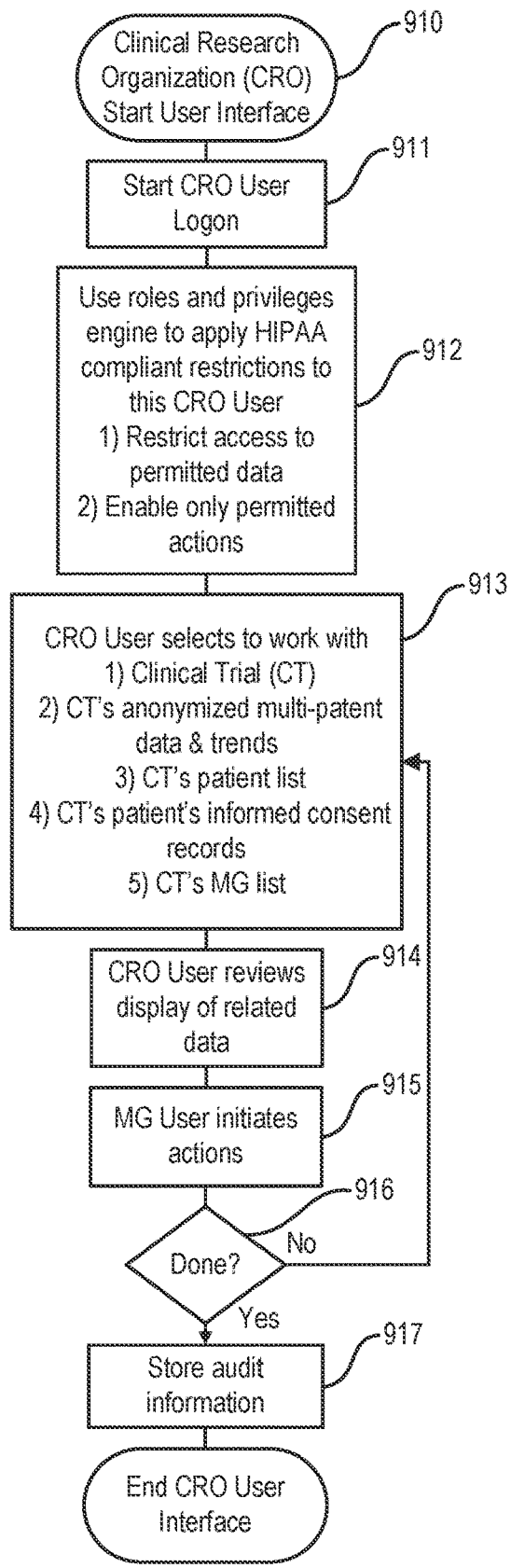
FIG. 5F shows Server control flow for the Clinical Research Organization (CRO) User Interface.

FIG. 5F provides a flow diagram of the process for using the Server Clinical Research Organization (CRO) User Interface 146. A CRO staff member 162 or a member of their staff with necessary credentials can logon in step 911 to the server 150 using the server CROUI via HIPAA compliant communication link 146. As part of the logon process, the CROUI looks at the credentials of the person logging on for their assigned roles and privileges (which may be group participation related) to apply HIPAA compliant restrictions to this particular CRO user that will 1) restrict access to permitted data and 2) enable only permitted actions, in step 912. Complying with aforementioned roles and privileges, the CRO User selects to work with 1) Clinical Trial (CT) configuration/management; 2) CT anonymized multi-patient data & trends; 3) the CT's patient list; 4) CT's patient informed consent records; or 5) CT's Medical Group (MB) list, in step 913. CRO User reviews display of related data in step 914. CRO User initiates actions as needed in step 915. If the CRO User is not done in step 916, the process returns to step 913 for more activities. When the CRO User is done in step 916, or after an inactivity timer expires, the CRO User logs out. Entered into the Audit log are a) the accesses to CT data storage; b) display of CT data; c) any related CT Events; and d) any CT activities, such that every activity on the server stores audit information in step 917 (further described below with regard to Audit 166).

Server Lead Administrator (LA) User Interface

FIG. 1B shows that the Lead Administrator (LA) User Interface (LAUI) 147 is the primary interface for Server Lead Administrator (LA) 164 (and LA's administrative staffs) to information on the server 150. There is normally a LA for each of the Clinical Research Organizations (CRO) or Medical Groups (MG) entities on the Server System. Notices of LA Events are managed through the LAUI. The LA 164 performs lead administrator activities for its assigned entity, either a CRO or a MG. The server 150 can provide the LA 164 for a CRO appropriate access to manage the other CRO staff and also the CT patient population. In a similar manner, the server 150 can provide the LA 164 for a MG appropriate access to manage the other MG staff and also the MG patient population (including proposing patents for CT enrollment). PHI-secure communication links 170 (not illustrated for brevity) are provided to LA staffs 164 for interaction with their respective CRO teams 162 or MG care providers 158.

Figure 5G:
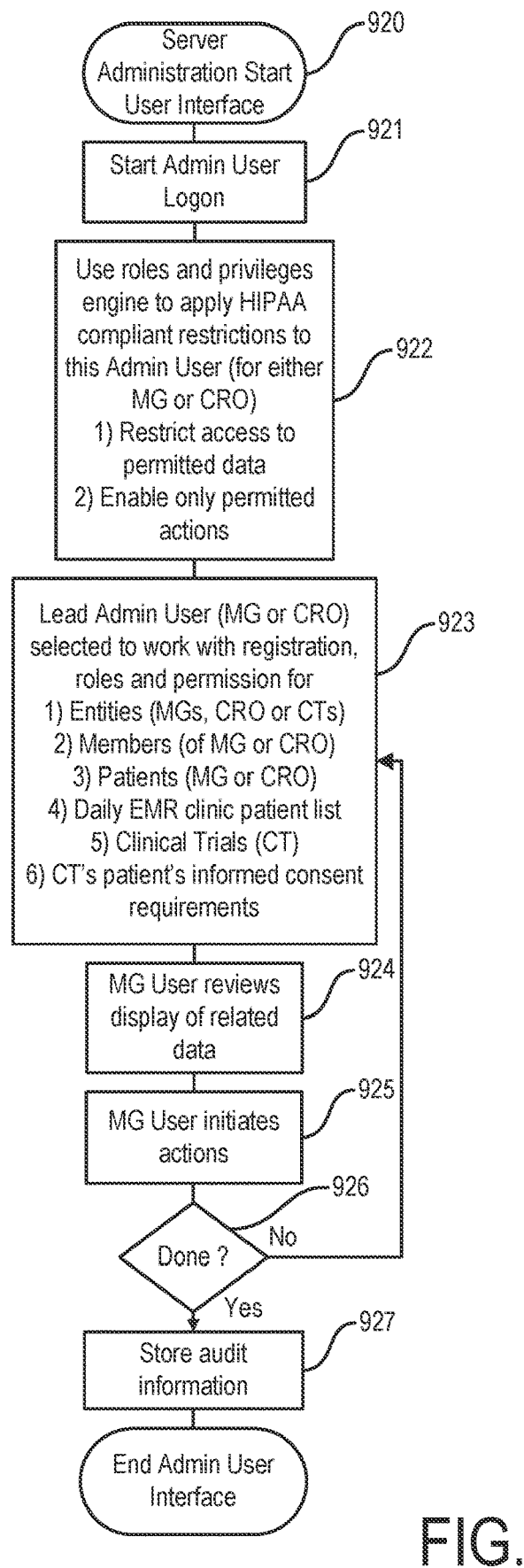
FIG. 5G shows Server control flow for the Server Lead Administrator User Interface for MG and CRO administrators.

FIG. 5G provides a flow diagram of the process for using the Server Lead Administrator User Interface (LAUI) 147. A LA 164 or a member of their staff with necessary credentials can logon in step 921 to the server 150 using the server LAUI via HIPAA compliant communication link 147. As part of the logon process, the LAUI looks at the credentials of the person logging on for their assigned roles and privileges (which may be group participation related) to apply HIPAA compliant restrictions to this particular LA user that will 1) restrict access to permitted data and 2) enable only permitted actions, in step 922. Complying with aforementioned roles and privileges, the LA user selects to work with 1) Entities (MGs, CROs or CTs) configuration/management; 2) Members (of MG or CRO); 3) Patient registration (MG or CT); 4) The MG's daily EMR clinic patient visit list; 5) Clinical Trials (CTs); or 6) CT's patient's informed consent requirements, in step 923. LA user reviews display of related data in step 924. CRO User initiates actions as needed in step 925. If the CRO User is not done in step 926, the process returns to step 923 for more activities. When LA user is done in step 926, or after the inactivity timer expires, the LA user is logged out. Entered into the Audit log are a) accesses to MG, CRO or CT data storage; b) display of accessed data c) any related MG, CRO or CT Events; and d) any MG, CRO or CT activities, such that every activity on the server stores Audit information in step 927 (further described below with regard to Audit 166).

Server Electronic Medical Record Interface (EMR)

FIG. 1B shows an event driven service interface 144 on the server 150 that enables an Electronic Medical Record (EMR) system 154 at a Medical Group to use standard protocols to log onto the server 150 with previously configured credentials. The EMR provides the server with a list of patients and related data that are scheduled to be seen in the MG clinic that day. The list is used to verify the patients are Registered Users 124 on the server 150 (or if permitted cause registration to occur) and, if desired, enable 124 to use a smart phone device in the clinic to take the Mobile App (MA) 116 test suite, with results delivered to the server 150. The information provided by the EMR is sufficient to register the patient on the server and enable the MA to be used to do "first time use" for a Registered User 124 if the eye care provider decides the MA test suite should be taken by that patient 124. The server responds to the EMR with confirmation of the patient list and indication as to which patients on the list are identified by the server 150 as existing MG patients and which are new MG patients on the server 150.

Regardless of the location where the User/patient uses the MA to take tests (at home or in the clinic), a MG member 158 can review the patient's test results on the server 150. The MG member can specify which test result reports should be transmitted in PDF format (other formats possible) to the EMR 154 for addition to the User/patient's EMR record.

Figure 5H:
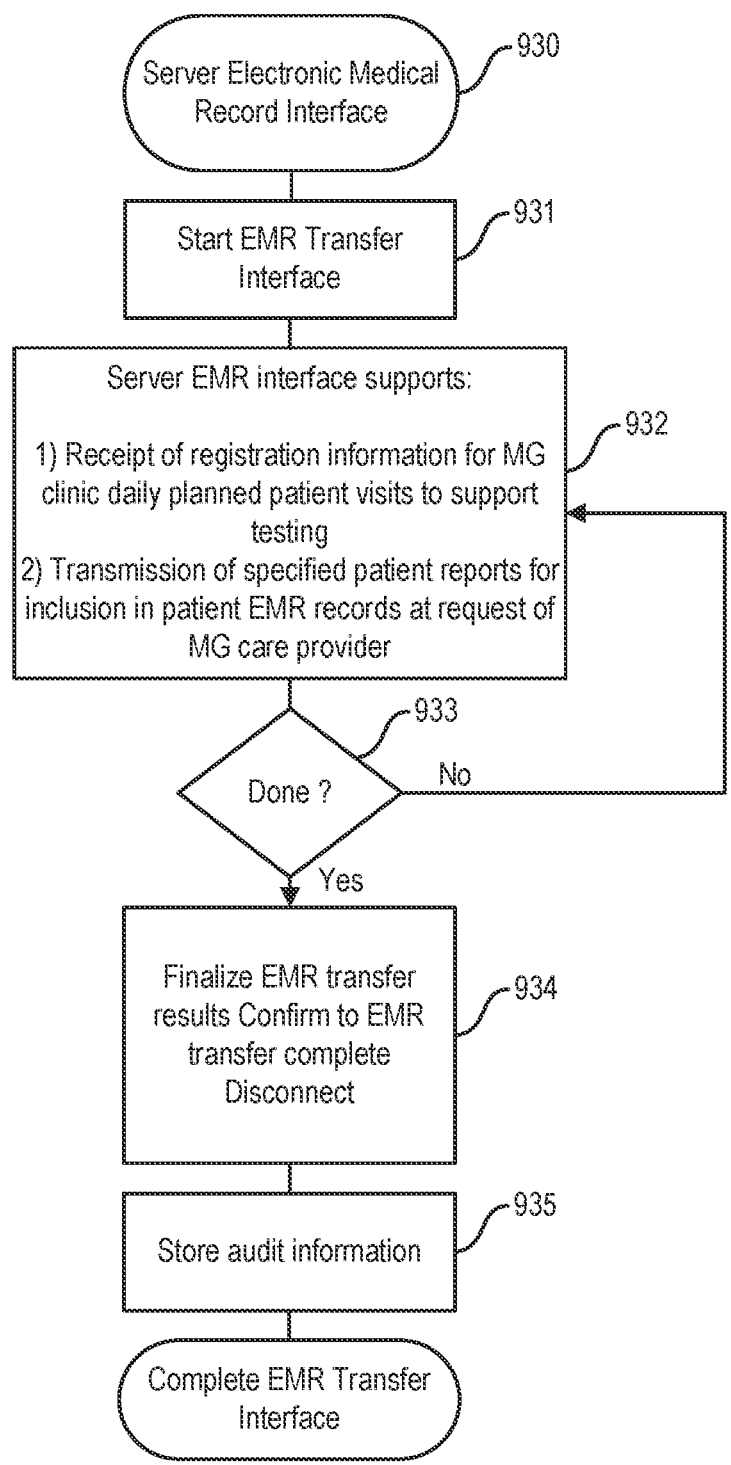
FIG. 5H shows Server control flow for the Server Interface services for the MG's Electronic Medical Record (EMR).

FIG. 5H provides a flow diagram for services provided to the EMR 154. Depending on the service to be performed, either the server 150 or the EMR can initiate the secure connection 144 and exchange authorization credentials in step 931. In step 932, the EMR services interface 144 can be invoked that may include: 1) Receipt by the server 150 from the EMR 154 of registration information for MG clinic daily planned patient visit list to support MA 116 testing, or 2) Server 150 transmission to EMR 154 of specified patient reports 138 for inclusion in the patient's EMR record at the request of the MG care provider 158. The server 150 checks to see if service requests are complete in step 933. If not, the process returns to step 932. If yes, server 150 causes the results of EMR interactions to be finalized in the server storage 934, the server confirms to EMR that the interaction is complete, and disconnects in step 934. Every activity on the Server stores Audit information in step 935 (further described below with regard to Audit 166).

Server Other Services (OS) Interface

As shown on FIG. 1B, a RESTful event driven service interface 149 on the server 150 enables Other Services (OS) 152 with proper credentials to interact with the server. It is important for the system and server to integrate comfortably into the MG or CRO environment. RESTful interface designs and related protocols are typically used for this purpose, and the server 150 supports this standard interface type to simplify extensions for integration with other systems where needed. (see https://restfulapi.net/). For example, a billing system could collect billable events from the Server 150. The OS 152 would use standard protocols to logon the server 150 with previously configured credentials. The OS uses, for example, a server transaction to request a list of billable events occurring after a certain date. The server 150 verifies the transaction request with the OS credentials and then provides the list of billable events after the date specified in the request.

Figure 5I:
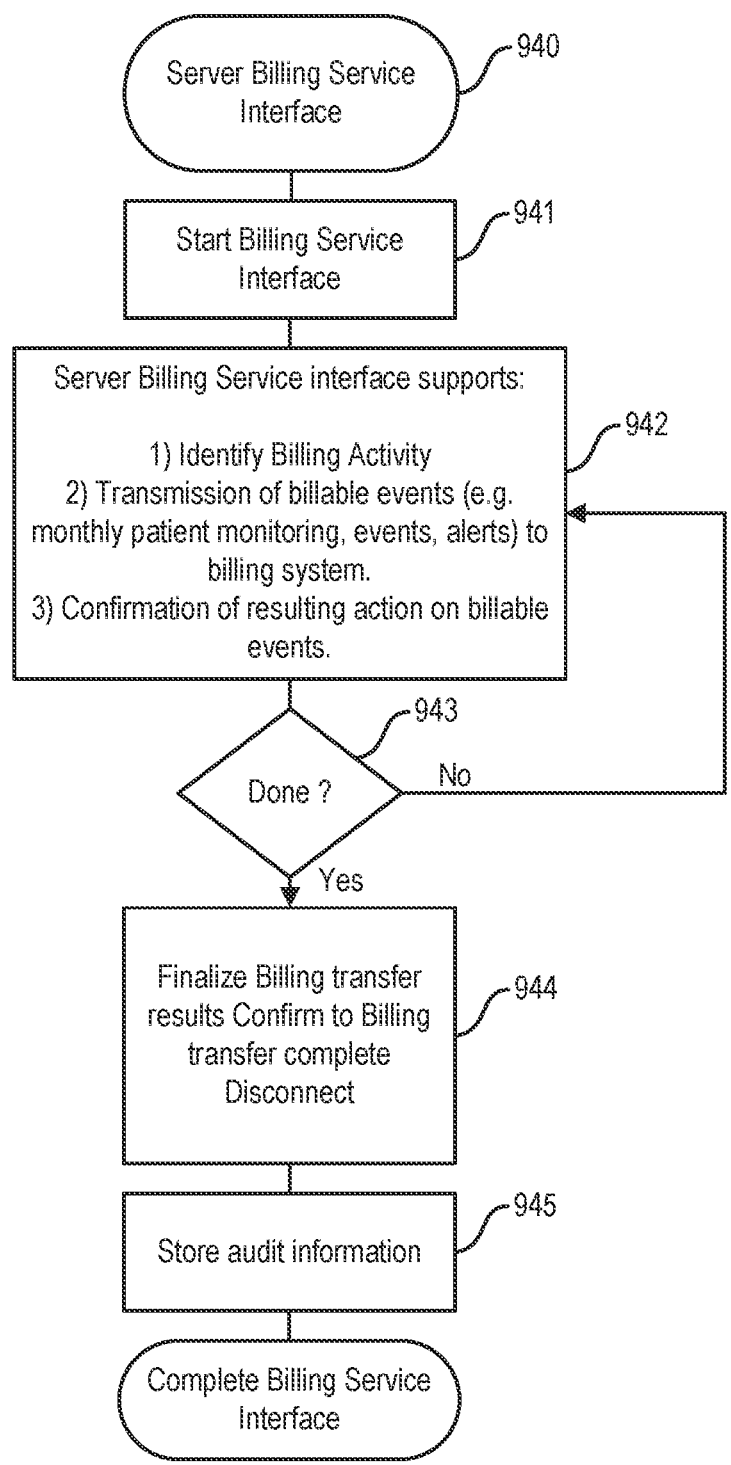
FIG. 5I shows Server control flow for the Server Interface services for other services, for example feeding home monitoring related activities monthly into the MG's Billing service.

FIG. 5I provides a flow diagram of the interface for services provided to the Other Services (OS) 152, in this example an external billing system. Depending on the service to be performed, either the server 150 or the OS 152 can initiate the secure connection 149 and exchange authorization credentials in step 941. The OS services interface 149 can be invoked in step 942 and may include transaction capabilities like: 1) Transmission of billable events to billing system 152, and 2) Confirmation of resulting action on billable events by billing system 152. The server 150 checks to see if service requests are complete in step 943. If not, the process returns to step 942 continues. If yes, the server 150 causes the results of OS interactions to be finalized in server storage, the server confirms to OS 152 that the interaction is complete, and disconnects in step 944. Every activity on the Server stores Audit information in step 945 (further described below with regard to Audit 166).

Server Audit (A) User Interface (Audit 166)

As shown on FIG. 1B, Audit (A) User Interface (AUI) 148 is the primary user interface for a system audit user 166 to access audit information on the Server 150. Notices of Audit Events and Audit Actions are managed through the AUI. For the system 190 and server 150 to be HIPAA and GDPR compliant, there must be a complete record of all system activities, including viewing PHI, actions with PHI, transmission of PHI to other systems, all server and system component maintenance actions, all physical and logical (network) access to the server and other system components. For each event, the audit logs will include the UTC date/time, what was accessed, by whom and what actions occurred. The AUI provides powerful standardized filtering and search capabilities that enable the Auditor to review events of interest efficiently. This is a comprehensive log and is implemented using ELK (a toolset also used by Netflix, Facebook, Microsoft, LinkedIn, Cisco and many other companies) (see https://opensource.com/article/18/9/open-source-log-aggregation-tool-s).

Figure 5J:
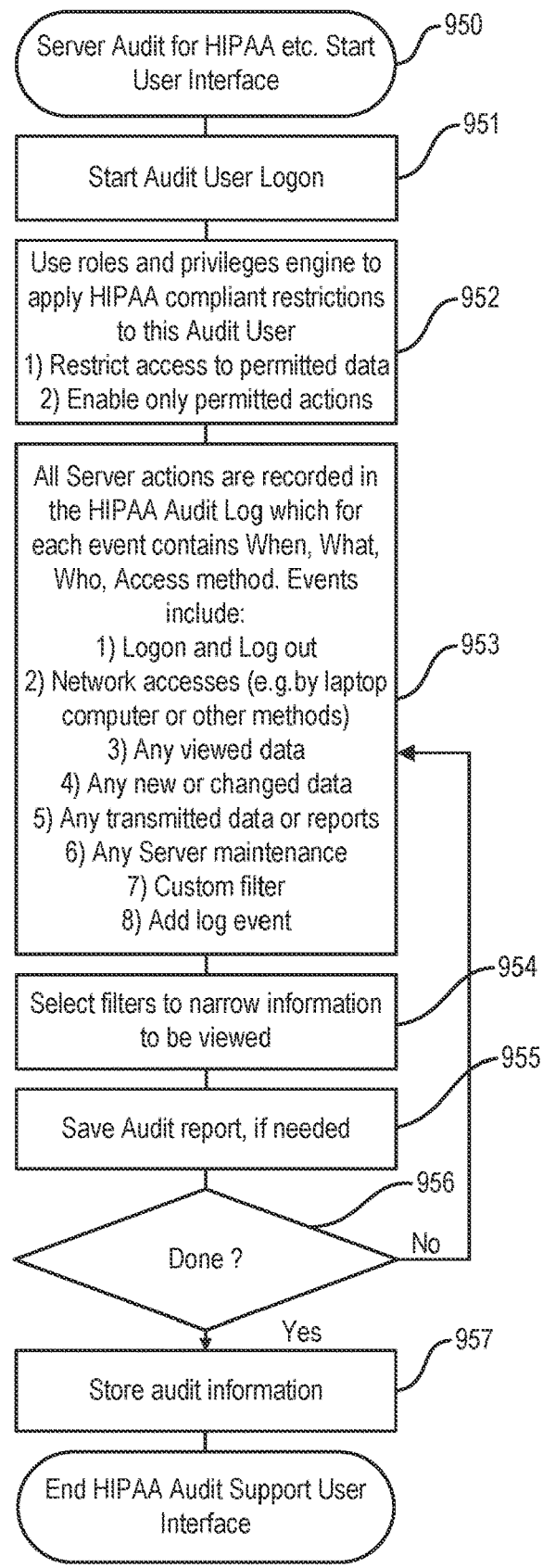
FIG. 5J shows Server control flow for the Server HIPAA Audit Support User Interface.

FIG. 5J provides a flow diagram of the process for using the Server Audit User Interface 148. An Auditor 166, or a member of their staff, with necessary credentials can logon to the Server 150 in step 951 using the server AUI via HIPAA compliant communication link 148. As part of the logon process, the AUI looks at the credentials of the person logging on for their assigned roles and privileges (which may be group participation related) to apply HIPAA compliant restrictions to this particular Audit user that will 1) restrict access to permitted data, and 2) enable only permitted actions, in step 952. Complying with aforementioned roles and privileges, the Audit User selects to filter for common events 1) Logon and Log out; 2) Network accesses (e.g. by laptop computer or other methods); 3) Any viewed data (option to be patient specific); 4) Any new or changed data; 5) Any transmitted data or reports; 6) Any server maintenance; 7) Set customer filters; or 8) Add/flag log entries (not change or delete), in step 953. Filters are further refined to narrow results in step 954. The Audit report is saved, if needed, in step 955. If the Audit User is not done in 956, the process returns to step 953 for more activities. When the Audit User is done in step 956, or after the inactivity timer expires, the Audit User logs out. Every activity on the Server, including by the Audit User, enters into the Audit log a) accesses to user data storage; b) any related Events or Actions; and c) all audit queries made, reports or additions, such that every activity on the server stores Audit information in step 957.

Having describe the disclosed subject matter, what is claimed as new and desired to be secured by Letters Patent is:

1. A mobile computing device, comprising:
    a processor;
    a display;
    a user interface presented on the display including a touch interface; and
    a memory accessible by the processor for storing instructions, which when executed by the processor causes the processor to:
        initiate a first vision-related test by presenting a series of grids individually displayed one at a time on the display, each grid having a fixation point, wherein the series of grids comprises: a first grid having a first fixation point centrally disposed on the first grid; and a plurality of subsequent grids, wherein each subsequent grid comprises a second fixation point disposed near a peripheral edge of each of the plurality of subsequent grids, and receiving an input from a first user through the user interface in response to each of the series of grids;
        processes the input received from the first user through the user interface in response to each of the series of grids to generate results of the first vision-related test derived from the input; and
        present the results on the display.

2. The mobile computing device of claim 1, the first vision-related test selected from a plurality of vision-related tests including but not limited to a visual acuity test, a color vision test, a central vision test, a dexterity test, and a cognitive test.

3. The mobile computing device of claim 2, the central vision test comprising:
    wherein each grid being a square having a plurality of intersecting horizontal and vertical lines disposed symmetrically on the grid and dividing the grid into smaller squares each measuring 0.5 centimeters;
    for each grid presented, receiving a mark made by the user on the touch display to represent a vision defect if the vision defect is observed by the user when the user is focused on the fixation point;
    combining the series of marked grids into a single display; and
    storing results of the grid marking.

4. The mobile computing device of claim 3, the processor further configured to:
    receive a selection by the user of a first eye to test;
    communicate the results of the selection of the first eye to a server via a secure, HIPAA-compliant interface;
    generate an analysis of results of at least two vision-related tests of the first eye from the server, including a trend in the results of the vision related tests;
    receive a selection by the user of a second eye to test;
    communicate the results of the selection of the second eye to a server via a secure, HIPAA-compliant interface; and
    generate an analysis of results of at least two vision-related tests of the second eye from the server, including a trend in the results of the vision related tests.

5. The mobile computing device of claim 3, wherein the series of grids comprises five grids, each grid is a 10 row by 10 column grid, wherein a first grid of the five grids includes a first fixation point located in a center of the first grid, wherein each of the four remaining grids is designated for a different peripheral quadrant adjacent the first grid such that a top left grid has the first fixation point located at a bottom right of the grid, a top right grid has the first fixation point located at a bottom left of the grid, a bottom left grid has the first fixation point located at a top right of the grid, and a bottom right grid has the first fixation point located at a top left of the grid.

6. The mobile computing device of claim 3, the processor further configured to:
    send the results of the grid marking to a server via a secure, HIPAA-compliant interface; and
    generate a consistency score that describes how similar the marks are on each of the grids including an evaluation of a position of the marks relative to the fixation point.

7. The mobile computing device of claim 1, wherein the central vision test comprises a central 10 degree grid.

8. The mobile computing device of claim 1, the processor configured to:
    communicate the results to a server via a secure, HIPAA-compliant interface; and
    generate an analysis of results of at least two vision-related tests from the server, including a trend in the results of the vision related tests.

9. The mobile computing device of claim 1, the processor configured to:
    prepare a formatted report summarizing the results; and
    send the formatted report to at least one other device via a secure, HIPAA-compliant interface.

10. A vision testing process, comprising:
    verifying identity of a first user from a first mobile computing device running a vision-related testing application, wherein the first mobile computing device includes a display and a user interface presented on the display including a touch interface;
    initiating a first vision-related test by presenting a series of graphical images individually displayed one at a time on the display of the mobile computing device, and receiving user input from the first user through the user interface in response to each of the series of graphical images;
    the series of graphical images including five grids, each grid comprised of rows and columns of open squares, wherein a first grid of the five grids is a central grid for central vision testing and includes a central fixation point located in a center of the center grid, wherein four remaining grids comprise four quadrant grids with each of the four quadrant grids designated for a different quadrant relative to the center fixation point such that a top-left quadrant grid has a bottom-right fixation point located at the bottom right of the top-left quadrant grid, a top-right quadrant grid has bottom-left fixation point located at the bottom left of the top-right quadrant grid, a bottom-left quadrant grid has a top-right fixation point located at the top right of the bottom-left quadrant grid, and a bottom-right quadrant grid has a top-left fixation point located at the top left of the bottom-right quadrant grid;

processing the user input received from the first user through the user interface in response to the series of graphical images to generate results of the first vision-related test derived from the user input; and presenting the results of the first vision-related test.

11. The vision testing process of claim 10, wherein presenting the results of the first vision related test comprises a composite graphical grid display.

12. The vision testing process of claim 11, wherein the composite graphical grid display is a composite of the five grids.

13. The vision testing process of claim 10, wherein presenting the results of the first vision related test comprises a unidirectional chart.

14. The vision testing process of claim 13, wherein the unidirectional chart displays data in a downward direction.

15. The vision testing process of claim 10, wherein each of the bottom-right fixation point, bottom-left fixation point, top-right fixation point, and top-left fixation point correspond to the central fixation point.

16. The vision testing process of claim 10, wherein the central grid has a central overlap portion overlapping at least one quadrant overlap portion of one of the four quadrant grids, and further comprising comparing the central overlap portion to the at least one quadrant overlap portion, and determining, based on the comparison, if a condition is met based on a rule, and if a condition is met generating a notice.

17. The vision testing process of claim 16, further comprising, determining a grid marking consistency score.

18. The vision testing process of claim 16, wherein the condition is adjustable by a care provider.

19. The vision testing process of claim 10, wherein the central grid includes: a) a top-left overlapping portion overlapping a top-left quadrant grid overlapping portion of the top-left quadrant grid; b) a top-right overlapping portion overlapping a top-right quadrant grid overlapping portion of the top-right quadrant grid; c) a bottom-left overlapping portion overlapping a bottom-left quadrant grid overlapping portion of the bottom-left quadrant grid, and d) a bottom-right overlapping portion overlapping a bottom-right quadrant grid overlapping portion of the bottom-right quadrant grid, and further comprising, determining a grid marking consistency score based on comparison of the overlapping portions of the central grid with the overlapping portions of the quadrant grids.

20. The vision testing process of claim 10, wherein the user input includes at least one of crooked, double, and missingness categories, and the missingness categories include dark, heavy gray, medium gray, and light gray.

21. The vision testing process of claim 10, further comprising determining a trend from the user input, and wherein presenting the results of the first vision-related test comprises displaying the trend for evaluation by a care provider.

22. The vision testing process of claim 21, wherein the trend comprises a time trend over a time period, and the time period is selectable by a care provider.

\* \* \* \* \*